(12) United States Patent
Weppenaar et al.

(10) Patent No.: US 8,590,365 B2
(45) Date of Patent: Nov. 26, 2013

(54) PIPE SYSTEM, A GAS SENSING SYSTEM FOR A PIPE SYSTEM, AND A METHOD OF DETERMINING A GAS COMPONENT IN A CAVITY OF A PIPE

(75) Inventors: Nicky Weppenaar, Copenhagen (DK); Mikael Kristiansen, Hellerup (DK)

(73) Assignee: National Oilwell Varco Denmark I/S, Brondby (DK)

( * ) Notice: Subject to any disclaimer, the term of this patent is extended or adjusted under 35 U.S.C. 154(b) by 404 days.

(21) Appl. No.: 12/995,740

(22) PCT Filed: Apr. 22, 2009

(86) PCT No.: PCT/DK2009/050093
§ 371 (c)(1),
(2), (4) Date: Dec. 2, 2010

(87) PCT Pub. No.: WO2009/146710
PCT Pub. Date: Dec. 10, 2009

(65) Prior Publication Data
US 2011/0154884 A1 Jun. 30, 2011

Related U.S. Application Data

(60) Provisional application No. 61/101,009, filed on Sep. 29, 2008.

(30) Foreign Application Priority Data

Jun. 3, 2008 (DK) ................................. 2008 00766
Sep. 26, 2008 (DK) ................................. 2008 01338

(51) Int. Cl.
*G01N 21/00* (2006.01)

(52) U.S. Cl.
USPC ....................................................... 73/24.02

(58) Field of Classification Search
USPC ............................................. 73/24.01, 24.02
See application file for complete search history.

(56) References Cited

U.S. PATENT DOCUMENTS 4,713,540 A * 12/1987 Gilby et al. .............. 250/227.21
4,817,413 A    4/1989 Asano et al.

(Continued)

FOREIGN PATENT DOCUMENTS

| DK | PA 2006 01706 A | 12/2006 |
|----|-----------------|---------|
| DK | PA 2007 01203 A | 8/2007  |
| WO | 03/056313 A1    | 7/2003  |
| WO | 2004/085905 A1  | 10/2004 |

OTHER PUBLICATIONS

Filus, et al., "A Novel Apparatus Based on a Photoacoustic Gas Detection System for Measuring Permeation Parameters of Polymer Samples," Polymer Testing, Elsevier, vol. 26, No. 5, Jun. 28, 2007, pp. 606-613.

(Continued)

*Primary Examiner* — Hezron E Williams
*Assistant Examiner* — Nathaniel Kolb
(74) *Attorney, Agent, or Firm* — Pearne & Gordon LLP

(57) ABSTRACT

The invention relates to a pipe system comprising a pipe, a gas sensing station and a remote output system. The pipe comprises a pipe gas cavity, such as an annulus, extending lengthwise in part or all of the length of the pipe; the gas sensing station comprises a sensing gas cavity which is in gas communication with the pipe gas cavity: The sensing gas cavity comprises a photoacoustic spectroscope. The pipe system comprises at least one optical feeding fiber for feeding light to the photoacoustic spectroscope and a transmission path for transferring a signal from the photoacoustic spectroscope to the remote output system, the transmission path from the gas sensing station to the remote output system is an optical transmission path.

The pipe may for example be a flexible pipe e.g. an umbilical or a pipe for the transportation of crude oil from a well to an off shore or on shore station, for example a ship or a platform.

The gas sensing station may be integrated in the pipe, e.g. in an end fitting or it may be an external gas sensing station.

According to a high security embodiment of the invention it is desired that all energy transported between the remote output system and the gas sensing station is in the form of optical energy e.g. transported in one or more optical fibers. This embodiment provides a very safe and simultaneously well functioning system, with reduced risk of igniting burnable fluids and simultaneously with a high signal-to-noise quality.

36 Claims, 14 Drawing Sheets

(56) References Cited

U.S. PATENT DOCUMENTS

| | | | |
|---|---|---|---|
| 5,125,749 A * | 6/1992 | Leugers et al. | 356/432 |
| 5,907,151 A * | 5/1999 | Gramann et al. | 250/214.1 |
| 6,123,114 A | 9/2000 | Sequin et al. | |
| 6,145,546 A | 11/2000 | Hardy et al. | |
| 6,412,825 B1 | 7/2002 | Langkjaer | |
| 6,472,614 B1 | 10/2002 | Dupont et al. | |
| 6,538,198 B1 | 3/2003 | Wooters | |
| 6,651,700 B1 | 11/2003 | Bastard et al. | |
| 6,668,866 B2 | 12/2003 | Glejbol et al. | |
| 6,923,477 B2 | 8/2005 | Buon et al. | |
| 7,024,941 B2 | 4/2006 | Andersen | |
| 7,234,492 B2 | 6/2007 | Bastard et al. | |
| 7,245,380 B2 | 7/2007 | Kosterev | |
| 7,296,480 B2 | 11/2007 | De Aquino | |
| 2001/0032892 A1 | 10/2001 | Brooks et al. | |
| 2002/0119271 A1 * | 8/2002 | Quigley et al. | 428/36.9 |
| 2005/0232703 A1 * | 10/2005 | Saint-Marcoux | 405/154.1 |
| 2006/0072869 A1 * | 4/2006 | Arias Vidal et al. | 385/13 |
| 2006/0266108 A1 * | 11/2006 | DiFoggio | 73/152.47 |

OTHER PUBLICATIONS

Ngai, et al., "Continuous Wave Optical Parametric Oscillator for Quartz-enhanced Photoacoustic Trace Gas Sensing," Appl. Phys. B 89, 123-128, 2007.

Kosterev, et al., "Ultrasensitive Gas Detection by Quartz-enhanced Photoacoustic Spectroscopy in the Fundamental Molecular Absorption Bands Region," Appl. Phys. B 80, 133-128, 2007.

Lewicki, et al., "QEPAS Based Detection of Broadband Absorbing Molecules Using a Widely Tunable, CW Quantum Cascade Laswer at 8.4 μm," 2007 Optical Society of America, Jun. 11, 2007, vol. 15, No. 12, Optics Express 7357-7366.

"Recommended Practice for Flexible Pipe," API Recommended Practice 17B, Third Edition, Mar. 2002.

"Specification for Unbonded Flexible Pipe," API Specification 17J, Twenty-Third Edition, Jul. 2008.

* cited by examiner

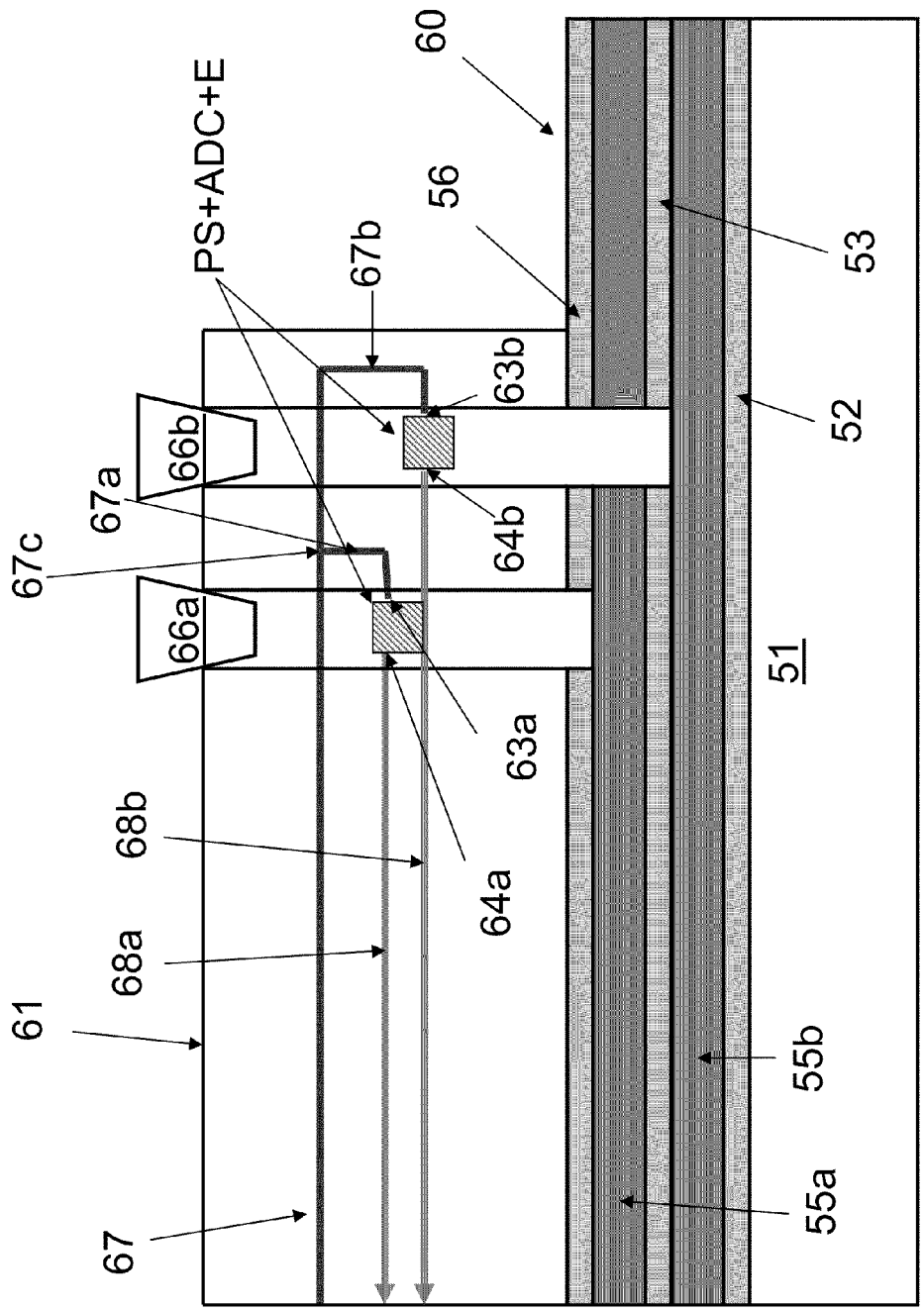

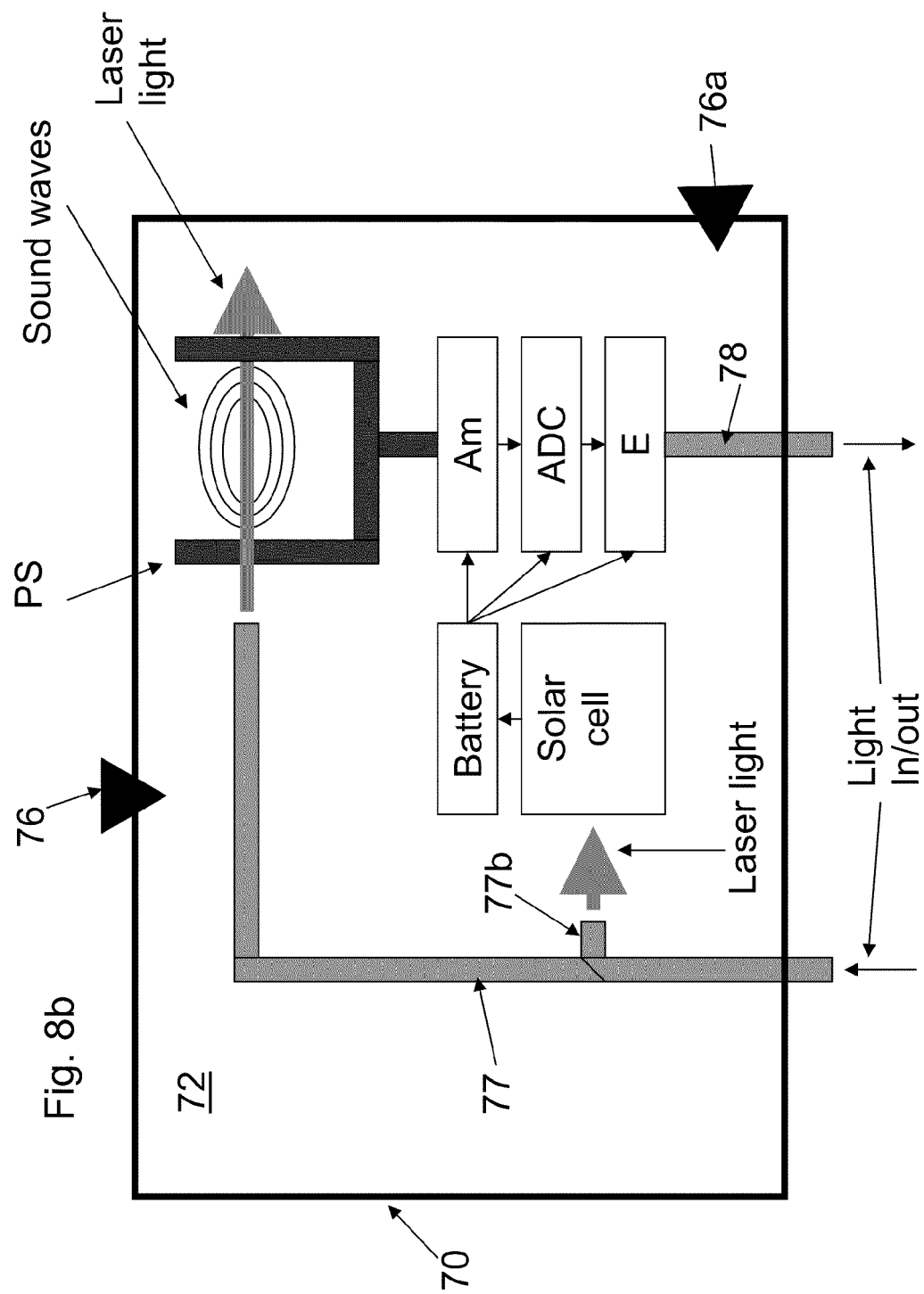

PIPE SYSTEM, A GAS SENSING SYSTEM FOR A PIPE SYSTEM, AND A METHOD OF DETERMINING A GAS COMPONENT IN A CAVITY OF A PIPE

TECHNICAL FIELD

The present invention relates to a pipe system, a gas sensing system for a pipe system and a method of determining a gas component in a cavity of a pipe.

BACKGROUND ART

Many types of pipe systems for transporting fluids, such as aggressive fluids, are known in the art, including both onshore and offshore pipe systems, such as pipes for transporting hydrocarbon containing fluids. Often the pipe system is subjected to high and often varying pressures both within its flow channel and if used offshore also from the surrounding water in which it is used or from being trenched and covered with rocks and other covering materials.

Pipes of this type often comprise several layers of materials for examples for providing the pipe with a sufficient strength during use or for providing other properties. Examples of pipes include rigid pipes e.g. double-sheath pipes also called double-walled pipes or pipe-in-pipe structures as described in any one of U.S. Pat. Nos. 665,700 and 7,234,492; umbilicals e.g. as described in U.S. Pat. Nos. 6,538,198 and 6,472,614, and flexible pipes such as a flexible pipe described in any one of U.S. Pat. Nos. 6,145,546, 6,123,114 and 6,668,866.

The present invention relates in particular to a system comprising a pipe comprising a flow channel and a gas cavity, typically an annular gas cavity surrounding the flow channel. Such an annular gas cavity is often equipped with a gas drainage valve in order to ensure that the pressure within the annular cavity does not exceed a certain selected pressure. Such a pipe with a gas drainage valve is for example described in U.S. Pat. No. 7,296,480. During use gas components such as gasses from the medium immediately surrounding the pipe (e.g. sea water) and/or from the fluid transported in the flow channel are penetrating into the annulus. Many of these fluid components are highly aggressive and in order to estimate the lifetime of the pipe it is desirable to know the qualitative and/or quantitative amount of such fluid components. Other less aggressive fluid components in the annulus can also be used in the analysis of the general state of the pipe as well as in the analysis of the fluid transported in the flow channel and the pressure/temperature conditions along the pipe. Furthermore a qualitative and/or quantitative determination of one or more fluid components in the annulus may be used to determine failure of the pipe in general such a local leakage or other fractures of one or more layers of the pipe. Usually the fluid components or at least a part of the fluid components are in gas form in the gas cavity.

The quantitative amount may be determined as the absolute quantitative amount e.g. per volume unit or it may be determined as the relative quantitative amount e.g. in relation to another fluid component, in relation to a set value, or in relation to any other value which makes sense to the skilled person.

It is therefore desirable to obtain qualitative and/or quantitative measurements of the gas components in the annulus of the pipe, with respect to one or more selected gas components and in particular one or more gas components.

WO 03/056313 describes a sensor system for use in the detection or measurement of at least one characteristic value relating to a chemical environment in a flexible pipe. The system comprises incorporating an optical fibre along a flexible pipe—e.g. in an armouring wire; letting a gas derived from the chemical environment diffuse into the optical fibre, thereby altering the optical properties of the optical fibre; detecting and analyzing light from the optical fibre so as to determine changes in the optical properties of the optical fibre due to the in-diffusion of said gas; and deriving said at least one characteristic value representing the chemical environment from the determined changes. This system, which has never been used in practice in a flexible pipe, is however fairly complicated to use as it reacts relatively slowly and it is difficult to obtain separate determination of desired fluid components.

The traditional method of determining fluid components from the fluid in the annulus is still to take out samples at regular intervals and to test them in the laboratory.

The object of the invention is therefore to provide a pipe system comprising a pipe comprising a flow channel and a gas cavity, typically an annular gas cavity surrounding the flow channel and which comprises a safe and simple arrangement for obtaining qualitative and/or quantitative determinations of one or more selected gas components in the gas cavity.

DISCLOSURE OF INVENTION

This object has been achieved by the invention as it is defined in the claims.

In the claims the term "as claimed in any one of claims X-Y" means as claimed in at least one of the claims X-Y. Accordingly the term "as claimed in any one of the preceding claims" means as claimed in at least one of the preceding claims.

As it will be clear to the skilled reader the invention and embodiments of the invention provide several additional benefits which are explained in the following.

The pipe system comprises a pipe, a gas sensing station and a remote output system. The pipe comprises a pipe gas cavity extending lengthwise in part or all of the length of the pipe. The gas sensing station comprises a sensing gas cavity which is in gas communication with the pipe gas cavity, the sensing gas cavity comprises a photoacoustic spectroscope, the pipe system comprises at least one optical feeding fiber for feeding light to the photoacoustic spectroscope and a transmission path for transferring a signal from the photoacoustic spectroscope to the remote output system. The transmission path from the gas sensing station to the remote output system is an optical transmission path.

According to the invention the inventors have thus provided a pipe system in which quantitative and/or qualitative determinations of the gas in a gas cavity can be performed in a very simple way with low risk of ignition of burnable fluids and without the need of withdrawing samples and carrying them to a laboratory. Even though the gas cavity in a pipe e.g. an annular gas cavity is often very small and typically comprises armouring elements, the system of the present invention can provide virtually on the spot determinations of the gas in a gas cavity of the pipe. Furthermore the determinations have shown to be very reliable and to be very insensitive to noise.

The pipe of the system may in principle be any kind of pipe comprising one or more gas cavities extending lengthwise in the pipe such as the pipes discussed in the background art section above, e.g. a pipe selected from rigid pipes e.g. double-sheath pipes also called double-walled pipes or pipe-in-pipe structures as described in any one of U.S. Pat. Nos. 665,700 and 7,234,492; umbilicals e.g. as described in U.S. Pat. Nos. 6,901,968, 6,538,198 and 6,472,614, and flexible pipes such as a flexible pipe described in any one of U.S. Pat. Nos. 6,145,546, 6,123,114 and 6,668,866.

The term "gas cavity" as used herein accordingly should be construed to mean a gas cavity extending lengthwise in the pipe in at least a length of the pipe which is about 1 meter or longer, usually at least half or essentially all of the length of the pipe.

The invention is particularly useful in situations where the pipe is an off shore pipe.

The skilled person has a general knowledge of such types of pipes and he know that any gas cavities in such pipes, in particular off shore pipes are very small and often comprises enforcing material (e.g. steel wires) which makes it very difficult to perform measurements on the spot, both due to lack of space, but also due to the risk of destroying sensitive sensor equipment, which is often fairly expensive. The gas cavity is preferably a cavity formed between coaxial layers of materials providing a barrier to the transport of gas. The solution of the present invention has shown to overcome such barriers for obtaining virtually on the spot gas determinations.

In one embodiment the pipe is a flexible pipe. The individual layers of the flexible pipe may e.g. be as described in "Recommended Practice for Flexible Pipe API 17B, Mar. 1, 2002" and "Specification for Unbonded Flexible Pipe 17J, Nov. 1, 1999" or any updated versions thereof.

The above-mentioned type of flexible pipes is used, among other things, for off-shore as well as some on-shore applications for the transport of fluids and gases. Flexible pipes can e.g. be used for the transportation of fluids where very high or varying water pressures exist along the longitudinal axis of the pipe, such as riser pipes which extend from the seabed up to an installation on or near the surface of the sea, pipes for transportation of liquid and gases between installations, pipes which are located at great depths on the seabed, or between installations near the surface of the sea. Such pipes are herein also referred to as harvesting pipes.

An umbilical is a type of flexible pipe which is used for the transport of process liquids and hydraulic oil and for carrying light and power from an installation positioned at the surface of the sea and down to the oil wells on the seabed. Umbilicals are not directly involved in the transport of oil and gas, but may be necessary for the supply of the process liquids which, as mentioned, are to be used for the recovery of oil, as well as for the running of hydraulic pipes, electrical wires, fibre optics, etc. An umbilical may be combined with an oil/gas transporting pipe e.g. a riser to form an integrated production umbilical or an integrated service umbilical.

In one embodiment of the invention the pipe is an umbilical. The umbilical may be constructed as the flexible pipe described below wherein the central part of the pipe enclosed by an internal sheath comprises one or more elements for the transport of process liquids and hydraulic oil and for carrying light and power from an installation positioned at the surface of the sea and down to the oil wells on the seabed.

In one embodiment the pipe is a flexible pipe comprising at least two unbonded layers, preferably the pipe comprises from inside out an internal sheath, one or more armouring layers and an outer sheath, said internal sheath preferably forming a resistance or barrier against the outflow of liquid fluid which is conveyed through the pipe through said flow channel, and said outer sheath preferably forming a barrier against ingress of liquid fluids.

The pipe may comprise an internal sheath and an outer sheath, and optionally one or more intermediate sheaths. Preferably at least two of the sheaths form a barrier against fluid, and the annular fluid cavity is provided between said two barrier sheaths. The two barriers providing sheaths are in the following referred to as barrier sheaths. The two barrier sheaths may e.g. be an internal sheath and an outer sheath, an internal sheath and an intermediate sheath, an intermediate sheath and an outer sheath and/or two intermediate sheaths.

A barrier sheath should herein be understood to mean a sheath which forms a resistance or a barrier against passage of a liquid fluid and/or a gas fluid, such that a different fluid composition can be maintained on the respective sides of the barrier sheath due to the barrier properties for example for at least 24 hours under ordinary use conditions of the pipe. The barrier sheaths will typically not provide a complete barrier against gas flow, but it is often preferred that the barrier sheaths provide at least a resistance against passage of gas. The barrier sheaths preferably form at least a resistance against hydrocarbons and/or sea water and/or one or more types of gas, such as oxygen, methane, hydrogen sulphides and carbon dioxides.

The pipe may comprise one or more flexible film or foil layers such as it is generally known in the art of flexible pipes. It is preferred that at least one of said one or more flexible film or foil layers forms a resistance or barrier against fluid, the annular fluid cavity being provided between said two barrier layers selected from barrier sheaths and foil/film barrier layers.

A foil layer means a layer of a metallic or metal containing material which is sufficiently flexible such that it does not significantly increase the total stiffness of the pipe. A film layer means a layer comprising a polymeric matrix in a layer, which layer is sufficiently flexible such that it does not significantly increase the total stiffness of the pipe. A foil/film barrier layer is a foil/film layer which forms at least a resistance, such as a resistance or a barrier against passage of a liquid fluid and/or a gas fluid, such that a different fluid composition can be maintained on the respective sides of the foil/film barrier layer due to the barrier properties for at least 24 hours under ordinary use conditions of the pipe. The foil/film barrier layer preferably forms a resistance or a barrier against hydrocarbons and/or sea water and/or one or more types of gas, such as oxygen, methane, hydrogen sulphides and carbon dioxides.

The annular fluid cavity (also called the annulus) may preferably extend along the length of the pipe, such as in a length of at least about 10 m, such as at least about 25 m, such as at least about 50 m, such as at least about 100 m, such as between about 50 and about 3000 m. The fluid cavity will often comprise one or more armouring layers of the pipe. In this situation it is in particular desirable to obtain measurement of aggressive fluids in the annulus.

In one embodiment of the invention the annulus comprises one or more optical fibers, such as an optical fiber for monitoring temperatures along the length of the pipe and or measuring mechanical properties along the length of the pipe. Flexible pipes comprising such optical fiber for monitoring temperatures along the length of the pipe and or measuring mechanical properties along the length of the pipe are for example described in applicant's U.S. Pat. No. 7,024,941 and co-pending applications DK PA 2006 01706 and DK PA 2007 01203.

The gas sensing station is separated from but in gas communication with said pipe gas cavity, preferably such that gas from the gas cavity flows directly into the gas sensing station e.g. via a pressure controlled valve. For security an on-of valve may additionally be arranged between the gas cavity and the gas sensing station. The valve may e.g. be as the valve described in the background art above.

Often the (annular) gas cavity will be equipped with a pressure adjusted valve gas exit to avoid that the pressure within the gas cavity increases over a certain selected pressure. Such pressure adjusted valve may for example be arranged in an end fitting coupled to one of the ends of the pipe.

In one embodiment one or more valves, e.g. pressure adjusted valve(s) are arranged in the sensing fluid cavity to control/adjust the pressure in said sensing fluid cavity.

In one embodiment one or more filters, e.g. filters preventing passage of liquids and/or selected gas components are arranged in the sensing fluid cavity to prevent selected components from exiting the sensing fluid cavity and/or to reduce the amount of selected components exiting the sensing fluid cavity.

The remote detector system comprises at least one light source optically connected to the photoacoustic spectroscope. The light source may preferably be optically connected to the photoacoustic spectroscope via at least one feeding fiber feeding light to the photoacoustic spectroscope. In one embodiment the feeding fiber optically connects the remote detector system with the gas sensing station. Inside the gas sensing station the light may be emitted directly to the photoacoustic spectroscope or it may be transported to the photoacoustic spectroscope by the same or another optical fiber and/or via one or more optically elements, such as one or more lenses and/or one or more mirrors. If desired it may additionally comprise one or more amplifiers and/or one or more splitters splitting the transported light into two or more light beams. In situations where the light is split into two or more light beams, one or more of the light beams may be used for supplying energy to one or more energy consuming elements inside the gas sensing station.

In one embodiment the remote output system comprises a light source optically connected to the photoacoustic spectroscope via said feeding fiber for feeding pulsed and/or modulated light into said photoacoustic spectroscope. The light may e.g. be sinusoidally modulated. Examples of useful modulations are described in U.S. Pat. No. 7,245,380.

In principle the light source can be any light source. In one embodiment the light source is selected to be capable of providing sufficiently energy to the photoacoustic spectroscope. In another embodiment an additional energy supply for supplying the sufficient or supplementary energy to the photoacoustic spectroscope.

Examples of light sources comprise a gas discharge lamp e.g. a xenon based light source, a laser, a light emitting diode (LED) and a semiconductor diode laser. It is preferred that the light source is a laser light source, such as a laser selected from supercontinuum lasers, said light source may for example be a broad spectered light source.

In one preferred embodiment the light source is a laser capable of supplying monochromatic Laser light.

In one preferred embodiment the light source comprises at least one tunable laser.

The optimal selection of light source depends on what it is desired to determine in the gas. The invention does not exclude that several light sources may be used.

The selected light source should preferably comprise wavelengths which are at least partly absorbable by the component which is to be determined in the gas, e.g. the light source should preferably comprise wavelengths which are at least partly absorbable by at least one of water vapour, methane ($CH_4$), hydrogen sulphide ($H_2S$), Carbon monoxide (CO), Carbon dioxide ($CO_2$), Oxygen ($O_2$) and hydrogen ($H_2$).

The light source may for example emit light comprising wavelengths in the range $10^{-10}$ to $10^{-2}$ meters, such as about $10^{-7}$ to about $10^{-5}$ meters e.g. about 1-10 μm, or such as about $10^{-9}$ to about $10^{-7}$ meters, e.g. about 400-600 nm.

The principle of the photoacoustic spectroscope is that a light beam is fed to a detection space comprising the gas to be examined to stimulate molecular excitation. Non-molecular decay and/or molecular rearrangements cause expansion and/or contractions whereby acoustic waves are generated. These acoustic waves can be determined in different way e.g. by a microphone and/or as described in U.S. Pat. No. 7,245,380.

The photoacoustic spectroscope preferably comprises a detection space. The detection space is a part of or the whole sensing gas cavity of the gas sensing station. The feeding fiber is preferably arranged to feed light to the detection space. The detection space is defined to be the space in which gas can be stimulated (preferably excitated) upon exposure to the emitted light. The sensing gas cavity of the gas sensing station is the gas containing cavity within the gas sensing station.

In one embodiment the photoacoustic spectroscope comprises an acoustic detector arranged to detect gas pressure changes occurring as a result of stimulation of the gas in the photoacoustic spectroscope with light. In principle any acoustic detector may be used provided it has a sufficient sensitivity. However, for off shore use the acoustic detector should be selected with great care. For example it has been found by the inventors that optical microphones are not the preferred choice due to inferior signal-noise properties.

In one embodiment the acoustic detector comprises at least one amplifier, e.g. in the form of a tuning fork comprising at least two prongs, the detection space comprises a space between said two prongs. The acoustic detector may in this embodiment for example comprise a microphone for detecting the gas pressure changes as sound waves. The microphone may preferably be an analogue microphone.

The tuning fork should preferably be selected to be resonant with the frequency of the pulsed or modulated light between two prongs of the tuning forks. The prongs vibrate in a symmetric vibration mode (the prongs move in opposite directions—away from and towards each other). The prong vibrations thereby amplify the signal without simultaneously amplifying any noise. Only symmetric vibrations generate a signal.

In one embodiment the microphone is in electrical communication with a transducer for converting electrical signals from said microphone into optical signals, said optical signals being transmitted along said optical transmission path.

Thereby the microphone can be an analogue microphone and the signal can be converted to an optical signal for transmission from the gas sensing station to the remote output system.

In this way all electrical units can be kept locally in the gas sensing station whereby risk of igniting burnable fluids is reduced to a minimum. The gas sensing station may for example be kept separated from the pipe as described below which provides additional security against undesired ignition.

Even though it may be desirably to keep all electrical locally in the gas sensing station for reducing risk of igniting burnable fluids, a electrical power supply may in one embodiment be incorporated for supplying the photoacoustic spectroscope with energy. Such electrical power supply should preferably be a low power supply as described further below. Since only small amounts of energy is required for the photoacoustic spectroscope, since the signal are optically transferred, any risk of igniting burnable fluids will still be reduced significantly.

In one embodiment the acoustic detector comprises at least one piezoelectric crystal for detecting the gas pressure changes. The piezoelectric crystal may for example be mounted on a tuning fork comprising at least two prongs to form a quarts enhanced tuning fork and the detection space preferably comprises a space between said two prongs. The acoustic detector may e.g. comprise a piezoelectric crystal as described in U.S. Pat. No. 7,245,380.

In a preferred embodiment the photoacoustic spectroscope is a quartz-enhanced photoacoustic spectroscope as described in U.S. Pat. No. 7,245,380 which additionally is in signal connection with an analogue-digital converter and an electromagnetic generator as described below, such that the obtained signal can be transported from the photoacoustic spectroscope to the remote output system in the form of electromagnetic waves, e.g. light.

Preferably the piezoelectric crystal is in electrical communication with a transducer for converting electrical signals from said piezoelectric crystal into optical signals, said optical signals being transmitted along said optical transmission path. In this way all electrical units can be kept locally in the gas sensing station whereby risk of igniting burnable fluids is reduced to a minimum. The gas sensing station may for example be kept separated from the pipe as described below which provides additional security against undesired ignition. Also in this embodiment electrical power may in one embodiment be supplied to the photoacoustic spectroscope and optionally connect elements via a wire without this results in any substantial risk of ignition of burnable fluids.

In one embodiment the acoustic detector comprises at least one analogue detector for detecting the gas pressure changes and this analogue detector is in electrical communication with a transducer for converting electrical signals from said analogue detector into optical signals, said optical signals being transmitted along said optical transmission path. It has been found by the inventors that the acoustic detector comprising at least one analogue detector for detecting the gas pressure changes provides good signal to noise sensitivity. Undesired noise may be at least partly defiltered e.g. by an analogue-digital converter or by another filter.

It is generally preferred that the system comprises a transducer for converting electrical signals into optical signals. The transducer preferably comprises an analogue-digital converter and an electromagnetic generator. The electromagnetic generator should preferably be a light emitter.

In a preferred embodiment the photoacoustic spectroscope comprises an acoustic detector comprising a tuning fork mounted with a piezoelectric crystal (i.e. a quarts enhanced tuning fork) in electrical communication with an analogue-to digital transducer, which analogue-to digital transducer is connected to a light emitter. The signal from the quarts enhanced tuning fork is obtained as an electrical signal from the quarts generated by the movements of the prong(s). By this embodiment a particularly good signal to noise sensitivity can be obtained. This embodiment is accordingly very useful in noisy environments, such as off shore areas with heavy sea, on and/or near platforms, and on and/or near ships.

As explained above the prongs vibrate in a symmetric vibration mode by activating of the light signal between the prongs. Only symmetric vibrations generate a signal. Noise outside the space between the prongs may result in asymmetrical vibrations of the prongs which will not result in any signal. In other words the noise will be at least partly defiltered.

The light emitter of the transducer may in principle be any light emitter emitting a light which can transmit the signal to the remote output system. Preferred light emitters include a laser preferably selected from a light-emitting diode (LED) and a semiconductor laser such as a Vertical cavity surface-emitting laser (VICSEL).

The pipe system may additionally comprise at least one amplifier for amplifying the signal from the photoacoustic spectroscope, such amplifier should be arranged in the gas sensing station.

In one embodiment comprising a photoacoustic spectroscope which comprises an acoustic detector comprising a piezoelectric crystal in electrical communication with an analogue-to digital transducer, which analogue-to digital transducer is connected to a light emitter, the amplifier is applied to amplify the electrical signal prior to converting the signal in the analogue-to digital transducer.

In another more preferred embodiment comprising a photoacoustic spectroscope which comprises an acoustic detector comprising a piezoelectric crystal in electrical communication with an analogue-to digital transducer, which analogue-to digital transducer is connected to a light emitter, the amplifier is applied to amplify the optical signal. This embodiment provides a beneficial amplification of the signal at the lowest possible energy consumption. The energy for the amplifier may in one embodiment be delivered by a light transmission and/or a battery and/or by electrical power as disclosed below. In one embodiment it is desired to provide as much as possible of the energy in the form of light, however, since the amount of energy required for the system is rather low other supply methods such by battery or as electrical power will also keep any risk of undesired ignition of burnable fluids to a minimum.

As indicated above the system of the invention may comprise one or more batteries. The battery or batteries is/are preferably local which herein means that the one or more batteries are located in the gas sensing station and preferably electrically insulated from the pipe.

Since the energy consuming elements in the gas sensing station such as a transducer and amplifier and/or a light emitter may be selected to use very little energy, the battery/batteries may be selected to be stationary long-life batteries. Alternatively the one or more batteries may be rechargeable batteries e.g. rechargeable by an energy supply such as a solar cell and/or an optical fiber.

In one embodiment the pipe system comprises a local battery arranged to feed energy for the transmission of signals from the gas sensing station to the remote output system. The local battery may e.g. be arranged to feed energy to a light emitter.

In one embodiment one or more local batteries are arranged to feed energy to at least one of an amplifier, an analogue-to-digital converter and a light emitter.

In one embodiment the pipe system comprises a power supply for supplying the photoacoustic spectroscope with electrical power e.g. as indicated above. Feeding energy to the photoacoustic spectroscope may be more reliable than by other means, and since the amount of power necessary is rather small—mainly because the signal transfer is provided optically—it will remain safe to supply this energy as electrical power. The power supply may be provided via an electrical wire. The may be explosion protected/fault current protected e.g. by providing it with an electrical short so that it doesn't ignite a hazardous atmosphere causing an explosion. Further more the wire may be physically protected e.g. by packing it totally or partly in one or more layers of steel, aluminium and/or fiberglass. In one embodiment the power supply has an effect of from about 0.1 to about 1 Watt. The power may e.g. be provided as a DC low current such as from about 1-50 V—e.g. from about 2 to about 10 V and a current of from about 10 to about 1000 mA, e.g. from about 50 to about 200 mA. The electrical power may be constantly turned on or it may be regulated to be turned on only with intervals in which measurements are performed.

In one embodiment the pipe system comprises an electrical power supply arranged to feed energy for the transmission of signals from the gas sensing station to the remote output system. The electrical power supply may e.g. be arranged to feed energy to a light emitter.

In one embodiment the electrical power supply is arranged to feed energy to at least one of an amplifier, an analogue-to-digital converter and a light emitter.

As mentioned above the photoacoustic spectroscope preferably comprises a detection space, and the optical feeding fiber preferably is arranged to feed light to stimulate (preferably excitate) gas (preferably at least one gas component to be determined) in the detection space.

In one embodiment said optical feeding fiber is arranged to feed light to at least one energy consuming element in the gas sensing station to provide said at least one energy consuming element with energy. The at least one energy consuming element may be any of the energy consuming elements in the gas sensing station e.g. selected from a laser, an amplifier and a transducer. The optical feeding fiber may comprise a splitter splitting the light beam to feed light to stimulate gas in said detection space and to feed light to one or more energy consuming elements e.g. via a rechargeable battery or for direct consumption of the one or more energy consuming elements. In one embodiment the optical feeding fiber is arranged to feed light to stimulate gas in the detection space, and the energy of the light emitted to the detection space is converted to electrical energy, e.g. by a solar cell, and the energy is supplied to one or more energy consuming elements.

In one embodiment the pipe system comprises at least one secondary optical feeding fiber arranged to feed light to at least one energy consuming element in the gas sensing station to provide said at least one energy consuming element with energy. The at least one energy consuming element may be any of the energy consuming elements in the gas sensing station e.g. selected from a laser, an amplifier and a transducer. The secondary optical feeding fiber may be as an optical feeding fiber described above, which optical feeding fiber, in case there is at least one secondary optical feeding fiber, is denoted "the first optical feeding fibre". The first and the secondary optical feeding fibers may be equal or different from each other. For simplicity the first and the secondary optical feeding fibers will often be selected to be equal, or if the requirement to the first optical feeding fiber due to required properties to stimulate desired molecules in the gas results in a rather expensive optical feeding fiber, a less costly optical feeding fiber may be selected for the one or more secondary optical feeding fiber.

In one embodiment the pipe system comprises a first optical feeding fiber and one secondary optical feeding fiber (also called the second optical feeding fiber) arranged to feed light to at least one energy consuming element in the gas sensing station to provide said at least one energy consuming element with energy.

According to the invention it is desired that the detected signal is transported from the gas sensing station to the remote output system in the form of electromagnetic waves, preferably optical signals, radio signals, microwave signals and/or infrared signals. Preferably all energy transported from the gas sensing station to the remote output system is the form of optical energy, the optical energy preferably being transported in one or more optical fibers.

In one embodiment of the invention it is desired that the detected signal is transported from said gas sensing station to said remote output system in the form of electromagnetic waves, preferably optical signals radio signals, microwave signals and/or infrared signals.

In one embodiment all energy transported between the one or more remote output systems and the one or more gas sensing stations is in the form of optical energy, preferably transported in one or more optical fibers and optionally one or more interposed mirrors and/or one or more interposed lenses.

Inside the gas sensing station optical energy may be transported by for example optical fibers, planar waveguides and/or via one or more mirrors and/or one or more lenses. The one or more lenses and or mirrors may for example be arranged to guide and/or to focus a light beam to the desired spot e.g. a solar cell or a detection space.

According to a high security embodiment of the invention it is desired that all energy transported between said remote output system and said gas sensing station is in the form of optical energy, the optical energy preferably being transported in one or more optical fibers. This embodiment provides a very safe and simultaneously well functioning system, with reduced risk of igniting burnable fluids and simultaneously with a high signal-to-noise quality.

According to another high security embodiment of the invention it is desired that except for a DC low power supply as described above, all energy transported between said remote output system and said gas sensing station is in the form of optical energy, the optical energy preferably being transported in one or more optical fibers. Also this embodiment provides a very safe and simultaneously well functioning system, with reduced risk of igniting burnable fluids and simultaneously with a high signal-to-noise quality, and reduced risk of malfunctioning do to lack of supplied energy.

The remote output system preferably comprises the necessary equipment for analyzing and storing the optical output from the photoacoustic spectroscope. Such analyzing/storing equipment is well known in the art. Additionally the remote output system may comprise other equipment for handling and manipulating the data, including alarm systems, benchmarking systems and other.

In one embodiment the remote output system comprises an analyzer optically connected to the photoacoustic spectroscope for receiving optical output from said photoacoustic spectroscope.

The analyzer should preferably be capable of analyzing at least a fraction of the light delivered from said photoacoustic spectroscope. The analyzer may comprise a computer.

In one embodiment the analyzer is capable of analyzing light from the photoacoustic spectroscope to detect the presence and preferably the amount of water vapour and/or one or more of the components selected from oxygen, hydrogen, methane, hydrogen sulphides and carbon dioxides.

In one embodiment the remote output system comprises a light source and an analyzer, the light source and said analyzer are optically coupled such that the gas sensing station is capable of comparing the wavelengths and/or intensities of the emitted light with the output from the photoacoustic spectroscope.

Generally it is desired that the remote output system is not placed too close to the gas sensing station or too close to the pipe.

In one embodiment at least one active element of the remote output system is placed at a distance from the gas sensing station which is at least about 2 m, such as at least about 5 m, such as at least about 10 m, such as at least about 25 m, wherein the active elements are selected from said light source and said analyzer.

In one embodiment the whole remote output system is placed at a distance from the gas sensing station which is at least about 2 m, such as at least about 5 m, such as at least about 10 m, such as at least about 25 m.

In one embodiment the whole remote output system is placed at a distance from the pipe which is at least about 2 m, such as at least about 5 m, such as at least about 10 m, such as at least about 25 m.

In principle the distance between the remote output system and the gas sensing station may be as long as desired. In certain situations the distance will be up to several kilometers, such as up to about 3 KM, such as up to about 2 KM, such as up to about 1 KM.

The remote output system may be provided in one unit, i.e. the elements of the remote output system are collected in a single unit. Alternatively the remote output system comprises two or more units placed side by side or at a distance from each other. In most situations it is preferred that the remote output system is in one unit, preferably provided in a laboratory or a control room.

One remote output system may be optically connected to two or more gas sensing station. In the same way one gas sensing station may be optically connected to two or more remote output systems.

Accordingly in one embodiment wherein the remote output system comprises at least one light source and at least one analyzer, the remote output system is optically connected to two or more gas sensing stations, and preferably the light analyzer is optically coupled to two or more photoacoustic spectroscopes. Thereby one analyzer may be used more effectively.

In one embodiment wherein the remote output system comprises at least two light sources and one, two or more analyzers, the remote output system may preferably be optically connected to two or more gas sensing stations.

In one embodiment wherein the pipe system comprises two or more remote output systems, said two or more remote output systems may or may not be interconnected, such as optically interconnected. Such interconnected remote output systems may be used for benchmarking data from different photoacoustic spectroscopes, and for example for reducing noise from measurements from photoacoustic spectroscopes placed close to each other but in different gas sensing stations.

In remote output systems, wherein the pipe system comprises two or more gas sensing stations with respectively one or more sensing gas cavities, the sensing gas cavities of said two or more gas sensing stations are in gas communication with one or more gas cavities.

In one embodiment wherein the pipe system comprises two or more gas cavities, said two or more gas cavities may be in gas communication with one or more sensing gas cavities. For example two gas cavities may be in gas communication with the same sensing gas cavity in a gas sensing station. The gas communication may be continuous or controlled by valves. In one embodiment the two gas cavities are by turn in gas communication with the same sensing gas cavity. Thereby measurements from two gas cavities can be obtained by one photoacoustic spectroscope.

One or more valves and/or a filter may be arranged in the sensing gas cavity to control and/or to adjust the pressure in said sensing gas cavity.

In one embodiment the pipe comprises an end fitting and the gas sensing station is integrated in this end fitting.

An end fitting is a fitting provided at the end of the pipe or a fitting connecting two length sections of the pipe to each other.

Such end fittings are generally known in the art. Examples of end fittings can be found in WO04085905, U.S. Pat. No. 6,412,825 and U.S. Pat. No. 6,923,477.

Usually the pipe will comprise an end fitting in each of its ends. The end fitting may e.g. be an ordinary end fitting which is usually adapted to connect the pipe to another unit e.g. to a ship or a plat form for ejecting the fluid passing through the flow channel of the pipe into a tank or similar. In one embodiment the end fitting is a double end-fitting arranged to be coupled to two pipes for connecting the pipes.

In one embodiment where the pipe comprises an end fitting, and the sensing gas cavity is provided in said end fitting (i.e. integrated into said end fitting), the sensing gas cavity is in gas communication with the gas cavity of the pipe connected to the end-fitting. In one embodiment a valve and/or a filter is arranged between the sensing gas cavity and the (preferably annular) gas cavity. In one embodiment a valve and/or a filter is arranged between the sensing gas cavity and an excess opening in the gas cavity through which gas can escape. By these various valves and/or filters, pressure and/or fluid composition can be adjusted in the sensing gas cavity.

In one embodiment the gas sensing station is external to the pipe, in the following called an external gas sensing station. This embodiment permits the pipe system of the present invention to be used in a very flexible manner. Furthermore the external gas sensing station may be connected to existing pipes, and even to pipes in the form of for example risers which have already been deployed. The gas sensing station may in this embodiment be incorporated into a box which may e.g. be adapted for mounting directly to the pipe e.g. to an end fitting of a pipe. Embodiments of the pipe system comprising an external gas sensing station are highly beneficial, because such external gas sensing station can be provided with extra electrical insulation and if desired also thermal insulation to minimize any risk of ignition and sparkling outside the gas sensing station. The gas sensing station may further be provided with a temperature sensor for detection of initiated fire or danger of fire, and further the gas sensing station may comprise a closure mechanism which completely closes the gas sensing station for inflowing gas in case of a rising temperature. Any risk of disastrous ignition of burnable fluids in the pipe or in contact with the pipe can be completely removed, since lack of feeding gas in the gas sensing station will choke any initiated fire in the gas sensing station.

In one embodiment where the pipe comprises an external gas sensing station the pipe further comprises an access opening into its (annular) gas cavity through which the external sensing gas cavity is in gas communication with this annular gas cavity. The access opening may preferably be provided with a valve and/or a filter e.g. as described above.

In one embodiment where the pipe comprises an external gas sensing station the pipe further comprises at least one end fitting, and the access opening into the annular gas cavity is provided via this end fitting.

In one embodiment where the pipe comprises an external gas sensing station the external gas sensing station is fixed to or is adapted to be fixed to said end fitting preferably by use of one or more of a snap-lock and a bolt-nut arrangement. This embodiment is particularly simple to mount, which additionally makes is simple to replace the external gas sensing station in case one or more units in the external gas sensing station should be damaged or in other way cease to work properly.

The end fitting may preferably be a terminating end fitting applied in the end of the pipe adapted to be connected to an off-shore station (off-shore installation), such as a platform or a ship.

In one embodiment where the pipe comprises an external gas sensing station the external gas sensing station is connected to the end fitting, via a tube fixed to respectively said gas sensing station and said end fitting. This embodiment may be very beneficial in situations where access to the pipe and the end fitting of the pipe is difficult or limited. The tube may e.g. be connected to one or both of the external gas sensing stations and the end fitting by for example a snap-lock and/or a bolt-nut arrangement.

As mentioned above it is desired that the pipe is a flexible pipe. The pipe may be an onshore pipe e.g. for transporting aggressive chemicals e.g. crude oil, cracked oil, gasses and similar.

The pipe system of the invention is in particular beneficial if the pipe is an offshore pipe, for example an offshore pipe applied to transfer a fluid from one offshore station, such as from the sea bed, to an onshore station or another offshore station, such as a platform or a ship. Offshore lines are often divided into two categories, namely flow lines for transporting fluids along the seabed, e.g. as trenched pipes or pipes placed onto the sea bed, and risers for use in transporting fluids vertically in the sea often from a seabed installation to a sea surface installation.

The pipe may be a flow line. However, preferably the pipe is a riser pipe.

In one embodiment where the pipe is a riser, the riser comprises an end fitting for connecting to an offshore station, preferably an surface offshore station, such as a platform or a ship, the fluid sensing station is integrated in the end-fitting or is in fluid communication with the (annular) gas cavity via this end-fitting, e.g. as described above, and the remote output system is placed at the surface offshore station—e.g. in a control room or a laboratory.

In one embodiment where the pipe is a riser, the riser comprises an end fitting, connecting two length sections of the pipe to each other. The pipe is further connected to a surface offshore station, such as a platform or a ship. The said gas sensing station is integrated in the connecting fitting or is in gas communication with the (annular) gas cavity via this end fitting, e.g. as described above, and the remote output system is placed at said surface offshore station.

The invention also relates to a gas sensing system for sensing a gas in a cavity of a pipe, preferably an annulus cavity of a pipe. The gas sensing system comprises at least one gas sensing station and a remote output system. The gas sensing station comprises a sensing gas cavity.

In the sensing gas cavity the system comprises a photoacoustic spectroscope. The remote output system comprises at least one light source and an analyzer, and the at least one light source is optically connected to the photoacoustic spectroscope for feeding light to said photoacoustic spectroscope. The photoacoustic spectroscope further is optically connected to the analyzer for analyzing signals from the photoacoustic spectroscope. The gas sensing station is arranged to be connected to a pipe with a gas cavity to provide a gas communication between the gas cavity and the sensing gas cavity.

The at least one light source should preferably be optically connected to the photoacoustic spectroscope by at least one optical feeding fiber.

Also it is preferred that the system comprises an optical transmission path for transferring a signal from the photoacoustic spectroscope to the remote output system, wherein the optical transmission path from the gas sensing station to the remote output system is provided by an optical fiber.

The various elements of the gas sensing system and their relations/interconnections with each other may be as described above for the pipe system, except that the sensing fluid cavity is not integrated in the pipe, but is an external part. For example the light source may be as described above, the photoacoustic spectroscope may be as described above, the analyzer may be as described above, the pipe structure may be as described above and the sensing gas cavity may be as described above except that it is not integrated in the pipe.

For example the light source comprises at least one of a gas discharge lamp e.g. a xenon based light source, a laser, a light emitting diode (LED) and a semiconductor diode laser, more preferably the light source is a laser such as a laser selected from supercontinuum lasers, said light source preferably being a broad spectered light source.

Also as mentioned above the gas sensing station may comprise one or more batteries and/or an electrical power supply for supplying energy to said photoacoustic spectroscope.

In one embodiment the light source is adapted to emit light comprising wavelengths which are at least partly absorbable by at least one of water vapour, methane ($CH_4$), hydrogen sulphide ($H_2S$), Carbon monoxide (CO), Carbon dioxide ($CO_2$), Oxygen ($O_2$) and hydrogen ($H_2$).

The gas sensing system may preferably be adapted to be connected to a pipe comprising an access opening into an annular gas cavity such as described above. The sensing gas cavity is adapted to be in gas communication with the gas cavity through said access opening.

The invention also relates to a method of determining a gas component in an annular fluid cavity of a pipe comprising the use of a pipe system as described above.

The term "gas component" is used to denote any component of the gas, such as atom components or molecular components.

The determination may in one embodiment be a qualitative determination of the presence of one or more components, preferably selected from the group of oxygen, methane, hydrogen sulphides and carbon dioxides either in gas form or when dissolved in water. These components are alone or in combinations the most aggressive ones in the transport of crude oils, and accordingly it is desired that the method includes determining at least qualitatively the presence of the major part, preferably all of said gas components.

The determination may in one embodiment be a quantitative determination of the amount of one or more components, preferably selected from the group of oxygen, methane, hydrogen sulphides and carbon dioxides. It is in this embodiment desired that the method includes quantitative determination of the major part, preferably all of said gas components.

The determination may be performed continuously or at predetermined intervals.

In one embodiment the system is connected to an alarm which is activated if the results deviate from a set point or deviate significantly from previous determinations.

BRIEF DESCRIPTION OF DRAWINGS

The invention will be explained more fully below in connection with a preferred embodiment and with reference to the drawings in which:

FIG. 7 is a schematic side view of a fourth pipe system of the invention.

FIG. 8b is a schematic view of a similar, but not identical photoacoustic spectroscope in a gas sensing station and the optical fibers for optical communication with a not shown remote output system.

Figure 1:
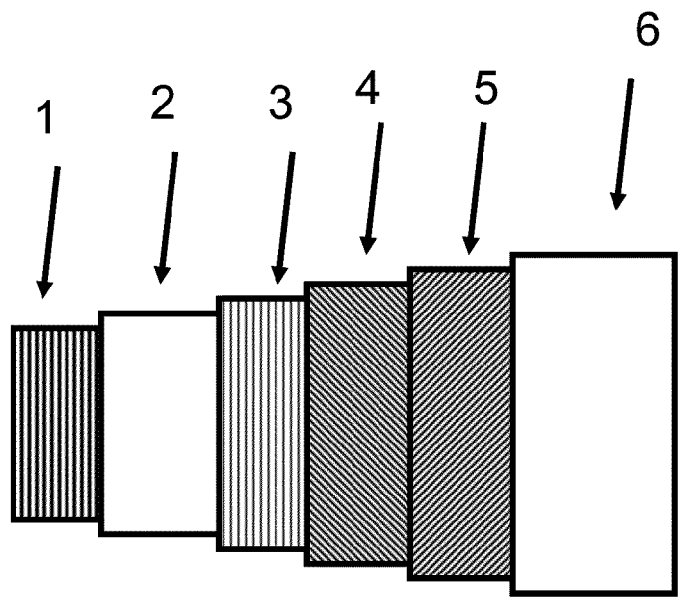
FIG. 1 is a schematic side view of a flexible pipe with a carcass.

Further scope of applicability of the present invention will become apparent from the detailed description given hereinafter. However, it should be understood that the detailed description and specific examples, while indicating some preferred embodiments of the invention, are given by way of illustration only, since various changes and modifications within the spirit and scope of the invention will become apparent to those skilled in the art from this detailed description.

The figures are schematic and simplified for clarity, and they merely show details which are essential to the understanding of the invention, while other details are left out. Throughout, the same reference numerals are used for identical or corresponding parts.

The flexible pipe shown in FIG. 1 comprises an internal sheath 2, often also called an inner liner, e.g. of cross linked PE. Inside the inner liner 2 the pipe comprises an inner armouring layer 1, called a carcass. On the outer side of the inner liner 2, the flexible pipe comprises three outer armouring layers 3, 4, 5. The inner armouring layer 3 closest to the inner liner 2 is a pressure armouring layer 3, made from profiles and/or strips wound at a steep angle to the centre axis of the pipe, e.g. close to 90 degrees. Around the pressure armouring layer 3, the pipe comprises a pair of cross wound tensile armouring layers 4, 5, made from wound profiles and/or strips. These tensile armouring layers 4, 5 are normally cross wound with equal or different angles of 70 degrees or less, typically 60 degrees or less, such as 55 degrees or less, such as between 20 and 55 degrees. The pipe further comprises an outer polymer layer (outer sheath) 6 protecting the armouring layer mechanically and/or against ingress of sea water.

Between the internal sheath 2 and the outer sheath is provided an annulus, also called an annulus cavity. In this annulus cavity the pressure armouring layer 3 and the tensile armouring layers 4, 5 are placed. The armouring layers are not fluid tight.

In case the flexible pipe is a harvesting pipe for transporting oil, gas or similar fluids from a well to a collecting unit such as a sea surface station (usually a ship or a platform), the core within the carcass is usually hollow for use as the transportation path. In the pipe in an umbilical the core within the carcass usually comprises a plurality of flexible plastic hoses and wires for transporting fluids, energy and other to the boring well.

Figure 2:
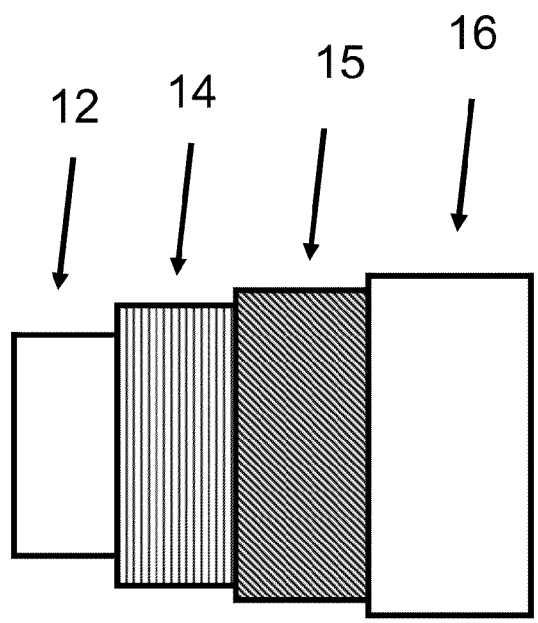
FIG. 2 is a schematic side view of a flexible pipe without a carcass.

FIG. 2 shows another pipe design. This flexible pipe comprises an inner liner 12 and a pair of outer armouring layers, 14, 15, in the form of profiles and/or strips wound around the inner liner 12. The two armouring layers are cross wound at an angle to the centre axis of the pipe of close to 55 degrees, typically one of the layers is wound at an angle slightly less than 55 degrees, e.g. between 52 and 55 degrees, and the other one of them is wound at an angle slightly more than 55 degrees e.g. between 55 and 57. The pipe further comprises an outer polymer layer 16 protecting the armouring layer mechanically and/or against ingress of sea water.

Between the internal sheath 12 and the outer sheath is provided an annulus, also called an annulus cavity. In this annulus cavity the outer armouring layers 14, 15 are placed. The armouring layers are not fluid tight.

Also this pipe may be a harvesting pipe or an umbilical as described above.

Figure 3:
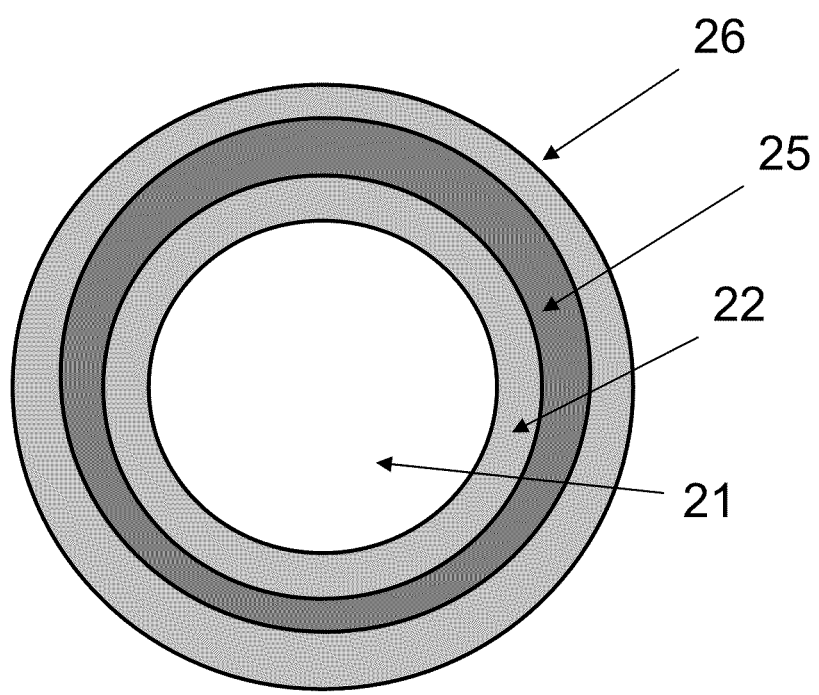
FIG. 3 is a cross-sectional view of a flexible pipe.

FIG. 3 shows in a schematic view a cross-sectional cut of a pipe. The pipe comprises an inner sheath 22 forming a flow channel 21 and an outer sheath 26. The inner sheath 22 and the outer sheath are barrier sheaths as defined above, and provide an annular cavity 25 between them. The annular cavity may comprise not shown armouring layers.

In a not shown variation of the pipe of FIG. 3 the pipe is an umbilical and the channel 21 comprises a plurality of flexible plastic hoses and wires for transporting fluids, energy and other to the boring well.

The pipe of the pipe system of the invention may for example be as shown in any one of FIGS. 1-3.

Figure 4:
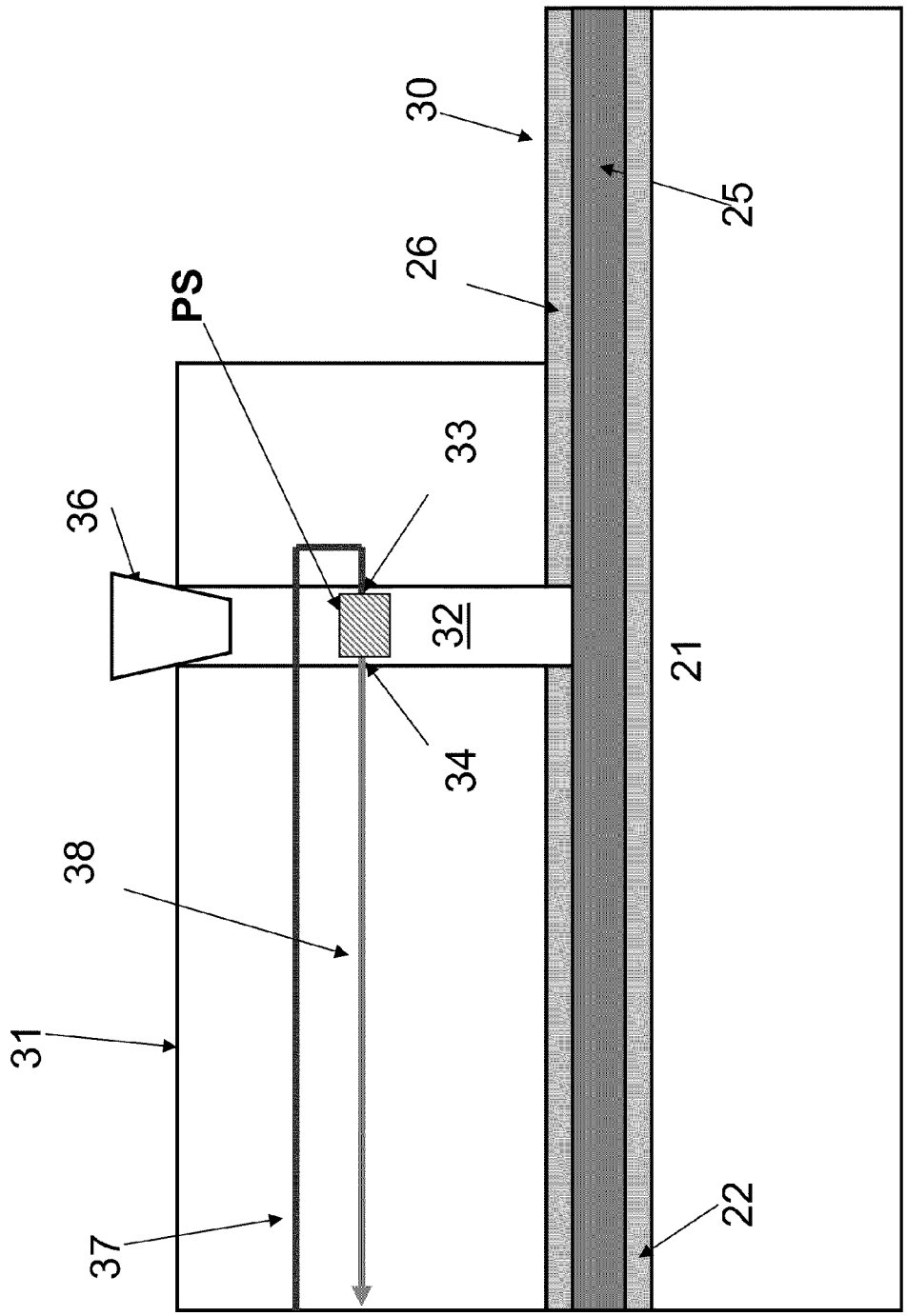
FIG. 4 is a schematic side view of a first pipe system of the invention.

FIG. 4 is a schematic side view of a first pipe system of the invention. The pipe system comprises a pipe 30 for example as shown in FIG. 3. The pipe comprises an end fitting 31 providing the gas sensing station, and comprising an integrated sensing gas cavity 32.

The sensing gas cavity 32 comprises a photoacoustic spectroscope PS. An optical feeding fiber 37 feeds light to the photoacoustic spectroscope PS, and the signal obtained in the photoacoustic spectroscope PS is transported in an optical transmission path (here an optical fibre) 38 to a not shown remote output system. The optical fibers 37 and 38 may be integrated into the material of the end-fitting 31 or they may be applied in suitable cavities, which should preferably be sealed off from the sensing gas cavity 32 so that gas within the sensing gas cavity 32 cannot escape in an uncontrolled fashion. The optical feeding fiber 37 feeds light to the photoacoustic spectroscope PS at a feeding point 33 within the sensing gas cavity 32 and the signal is transmitted to the optical fiber 38 at a transmission point 34 within the sensing gas cavity 32 so that all energy transport between the sensing gas cavity 32 and the remote output system is provided by optical fibers.

If the photoacoustic spectroscope has an electrical output an additional not shown transducer for converting the signal to an optical signal should be arranged between the photoacoustic spectroscope PS and the optical fiber 38. One possible operation of the photoacoustic spectroscope is described further below.

The sensing gas cavity 32 is in gas communication with the annulus 25 via an opening 35 in the pipe into the annulus 25. The sensing gas cavity comprises a valve 36 for adjusting and/or controlling the pressure in the sensing gas cavity 32. Simultaneously the valve 36 may ensure that the pressure within the annulus cavity 25 does not increase above a desired level.

The pipe system further comprises a not shown remote output system. The remote output system comprises a light source as described above for feeding light to the optical fiber 37. The remote output system further comprises an analyzer as described above for receiving the signals from the photoacoustic spectroscope PS via the optical fiber 38.

Figure 5:
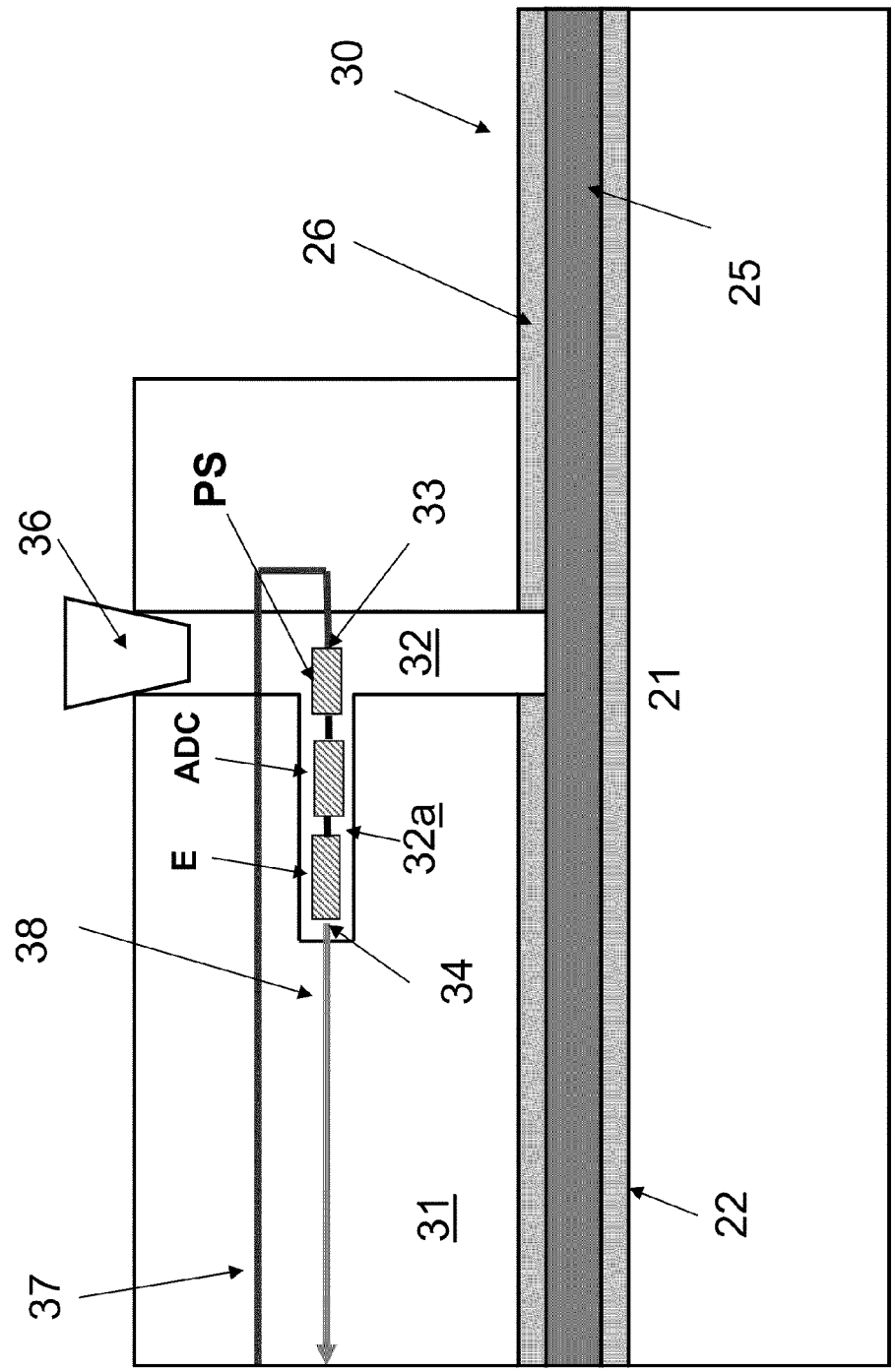
FIG. 5 is a schematic side view of a second pipe system of the invention.

FIG. 5 is a schematic side view of a second pipe system of the invention. The pipe system in FIG. 5 is similar to the pipe system shown in FIG. 4 except that the sensing gas cavity 32 comprises an additional section 32a in which the photoacoustic spectroscope PS, an analogue-to-digital converter ADC and a light emitter E are arranged. By this arrangement it is simpler to arrange the photoacoustic spectroscope PS in the sensing gas cavity 32 without requiring the end-fitting 31 to be substantially larger than the end-fitting used to day. Since the requirement to strength end fittings is very high, this configuration may additionally result in cost reduction without any substantially strength reduction. The photoacoustic spectroscope PS in FIG. 5 may preferably be a quartz enhanced photoacoustic spectroscope as described in U.S. Pat. No. 7,245,380.

Figure 6:
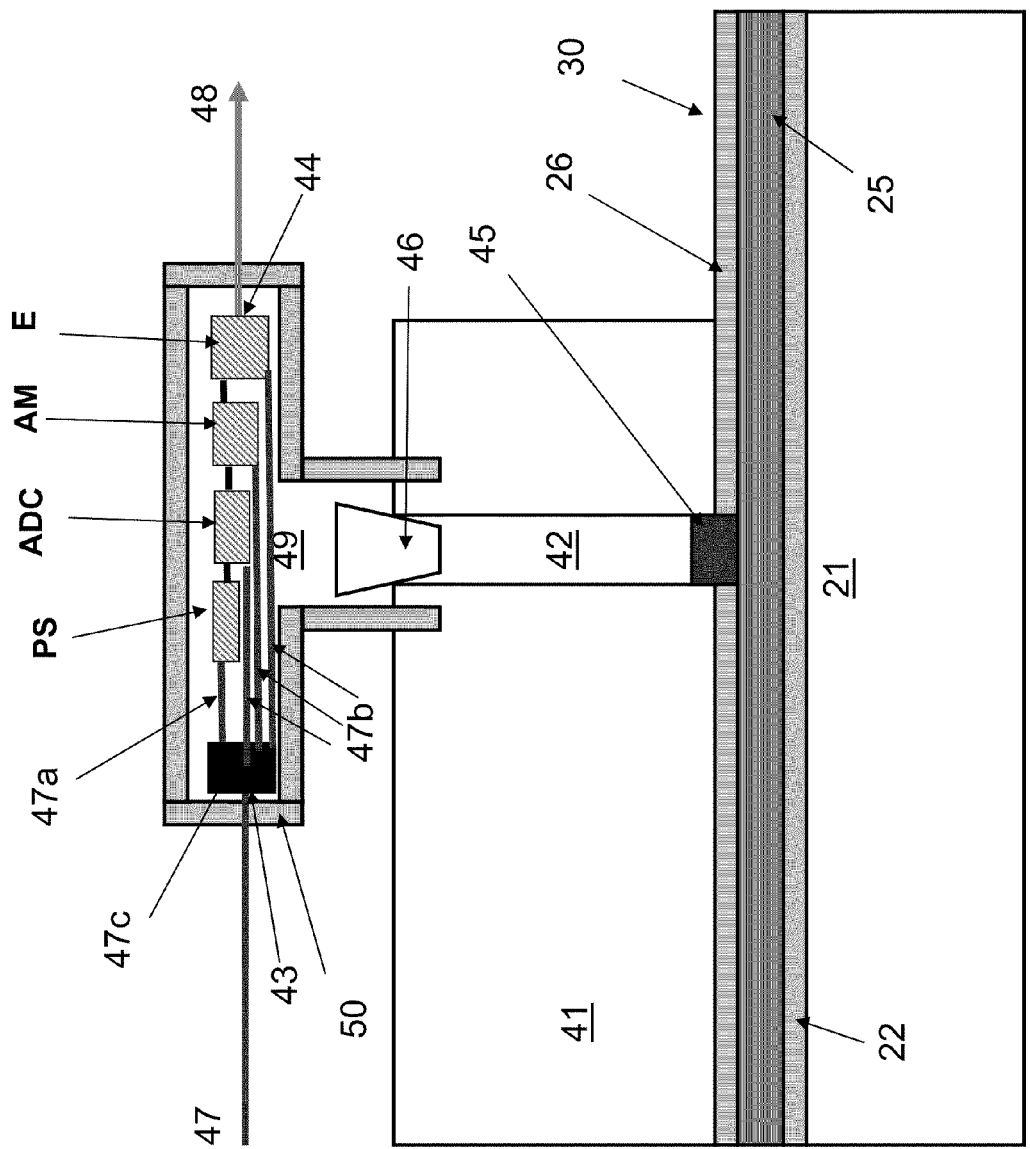
FIG. 6 is a schematic side view of a third pipe system of the invention.

FIG. 6 is a schematic side view of a third pipe system of the invention. The pipe system of FIG. 6 comprises a pipe 30 similar to the pipe in the pipe system shown in FIG. 4. The pipe comprises an end fitting 41, with an access channel 42 providing a gas access path to the annulus cavity 25. The pipe 30 comprises an access opening to the access channel 42 and a filter 45 is arranged in the access opening to prevent liquid and particles from escaping from the annular cavity 25. The pipe system further comprises a gas sensing station 50 placed externally to the pipe 30 and connected to the end-fitting 41 e.g. by use of a not shown bolt-nut arrangement.

The gas sensing station 50 comprises a sensing gas cavity 49 which is arranged to be in gas communication with the annular cavity 25 via the access channel 42 in the end fitting. In the passage between the end fitting access channel 42 and the sensing gas cavity 49 a valve 46 is arranged in order to adjust and/or control the pressure in the annular cavity 25 and optionally in the sensing gas cavity 49. The gas sensing station 50 further comprises a not shown valve to further adjust and/or control the pressure in the sensing gas cavity 49.

The optical feeding fiber 47 is transmitting light from a not shown remote output system and is feeding light into the sensing gas cavity 49 of the gas sensing station 50 at a feeding point 43 within the sensing gas cavity 49, and the obtained signal is transmitted to the optical fiber 48 at a transmission point 44 within the sensing gas cavity 49 so that all energy transport between the sensing gas sensing station 50 and the remote output system is provided by optical fibers.

The sensing gas cavity 49 comprises in signal communication a photoacoustic spectroscope PS, an analogue-to-digital converter ADC, an amplifier AM and a light emitter E.

The sensing gas cavity 49 further comprises a splitter 47c splitting the light from the optical feeding fiber 47, one feeding fiber 47a for feeding the photoacoustic spectroscope PS and three feeding fibers 47b for feeding energy to respectively the analogue-to-digital converter ADC, the amplifier AM and the light emitter E.

The pipe system in FIG. 6 further comprises a not shown remote output system. The remote output system comprises a light source as described above for feeding light to the optical fiber 47. The remote output system further comprises an analyzer as described above for receiving signals via the optical fiber 48.

FIG. 7 is a schematic side view of a fourth pipe system of the invention. The pipe system comprises a pipe 60 comprising two separate annulus cavities 55a, 55b provided by three barrier layers in the form of an inner sheath 52, forming a flow channel 51, an intermediate sheath 53, and an outer sheath 56. The annular cavities may comprise not shown armouring layers e.g. as explained above.

The pipe comprises an end fitting 61 with an integrated gas sensing station in the form of two integrated sensing gas cavities 62a, 62b.

In each of the sensing gas cavities 62a, 62b are a photoacoustic spectroscope PS, an analogue-to-digital converter ADC and a light emitter E. illustrated by a PS+ADC+FE-box.

Each PS+ADC+E-box is supplied by light from an optical feeding fiber 67 at respective feeding points 63a, 63b and the obtained signal is transmitted to the optical fibers 68a, 68b at respective transmission points 44a, 44b within the respective sensing gas cavities 62a, 62b so that all energy transport between the sensing gas sensing station and the remote output system is provided by optical fibers. In the shown embodiment the optical feeding fiber 67 comprises a splitter 67c, splitting the light into two for feeding both PS+ADC+E-boxes.

The two sensing gas cavities 62a, 62b respectively are in gas communication with the annulus cavities 55a, 55b via respective openings 54a, 54b in the pipe into the respective annulus cavities 55a, 55b. Each of the sensing gas cavities 62a, 62b comprise a valve 66a, 66b for adjusting and/or controlling the pressure in the respective sensing gas cavities 62a, 62b. Simultaneously the valves 66a, 66b may ensure that the pressure within the respective annulus cavities 55a, 55b, does not increase above a desired level.

The pipe system in FIG. 7 further comprises a not shown remote output system. The remote output system comprises a light source as described above for feeding light to the optical fiber 67 which comprises the splitter 67c. The remote output system further comprises at least one analyzer as described above for receiving light collected by the respective optical fibers 68a, 68b.

Figure 8A:
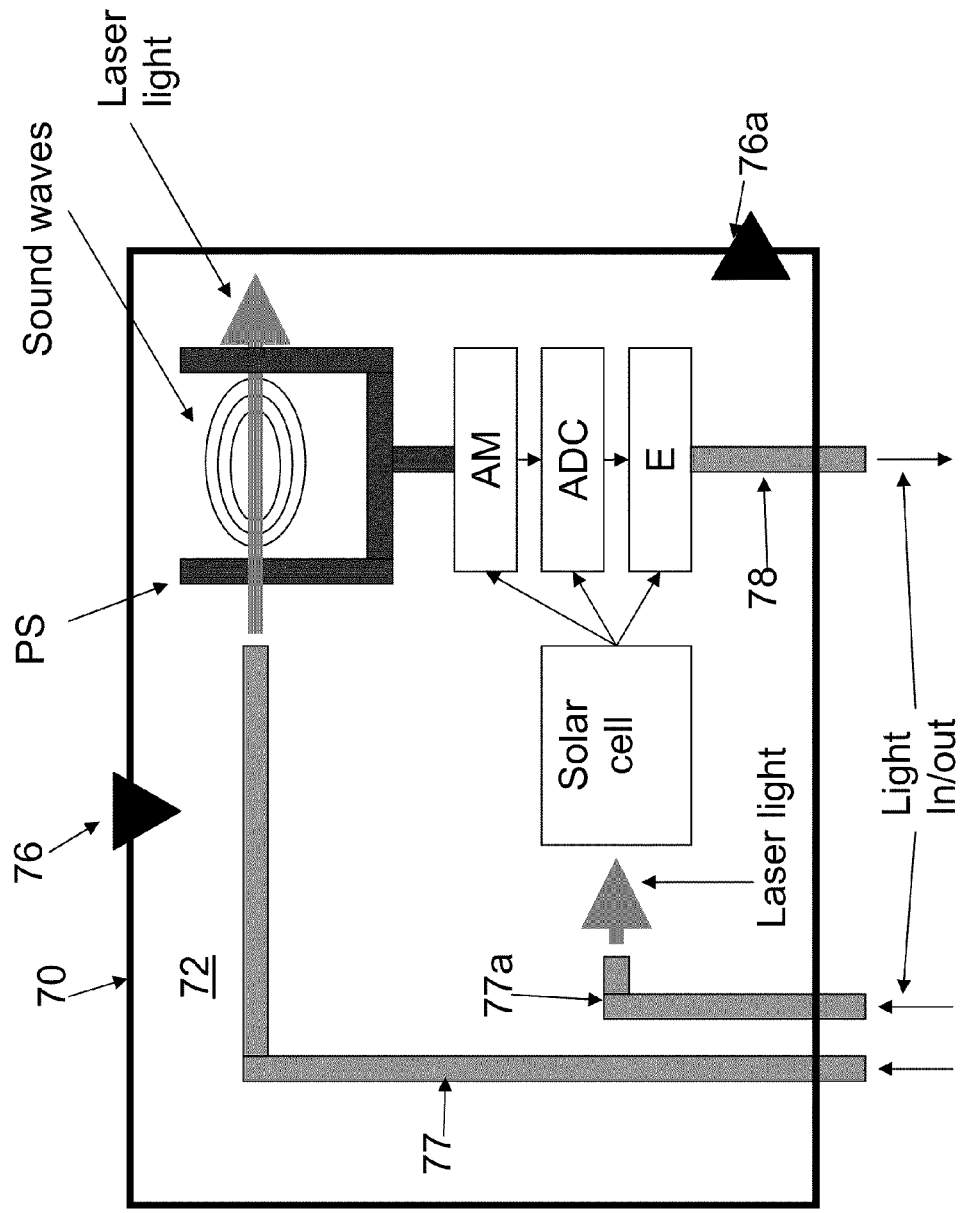
FIG. 8a is a schematic view of a photoacoustic spectroscope in a gas sensing station and the optical fibers for optical communication with a not shown remote output system.

FIG. 8a is a schematic view of a photoacoustic spectroscope in a gas sensing station and the optical fibers for optical communication with a not shown remote output system.

The gas sensing station 70 comprises a first vent 76 connected to a not shown pipe gas cavity for inflow of gas and a second vent 76a for outflow of gas. In the gas sensing station 70 is a sensing gas cavity 72 comprising a photoacoustic spectroscope PS comprising a quartz-enhanced tuning fork comprising two prongs, and in signal communication with an amplifier AM, an analogue-to-digital converter ADC and a light emitter E. The sensing gas cavity 72 further comprises a solar cell from which energy is fed to respectively the amplifier AM, the analogue-to-digital converter ADC and the light emitter E.

A first and a second optical feeding fiber 77, 77a transmit light from a not shown remote output system and feed light into the gas sensing station 70. The second optical feeding fiber 77a transmits light to the solar cell from where energy is fed to energy consuming units in the sensing gas cavity 72. The first optical feeding fiber 77 transmit laser light to the photoacoustic spectroscope PS. The laser light is emitted to stimulate the gas between the two prongs of the fork and sound waves are generated. The sound waves are amplified in the amplifier AM, converted in the analogue-to-digital converter ADC and transmitted via the light emitter E. and an optical fiber 78 to the remote output system.

All energy transport between the sensing gas station 70 and the remote output system is provided by optical fibers.

FIG. 8b is a schematic view of a similar, but not identical photoacoustic spectroscope in a gas sensing station and the optical fibers for optical communication with a not shown remote output system.

The photoacoustic spectroscope in a gas sensing station shown in FIG. 8b differs from the photoacoustic spectroscope in a gas sensing station shown in FIG. 8a in that it only comprises one optical feeding fiber 77 delivering light from the remote output system. This optical feeding fiber 77 comprises a splitter which splits off a part of the light to a secondary optical fiber 77b, which optical fiber 77b transmits light to the solar cell. The solar cell is connected to a battery and the light is used for recharging the battery. The battery is connected to energy consuming units in the sensing gas cavity 72 for feeding energy to them.

Figure 8C:
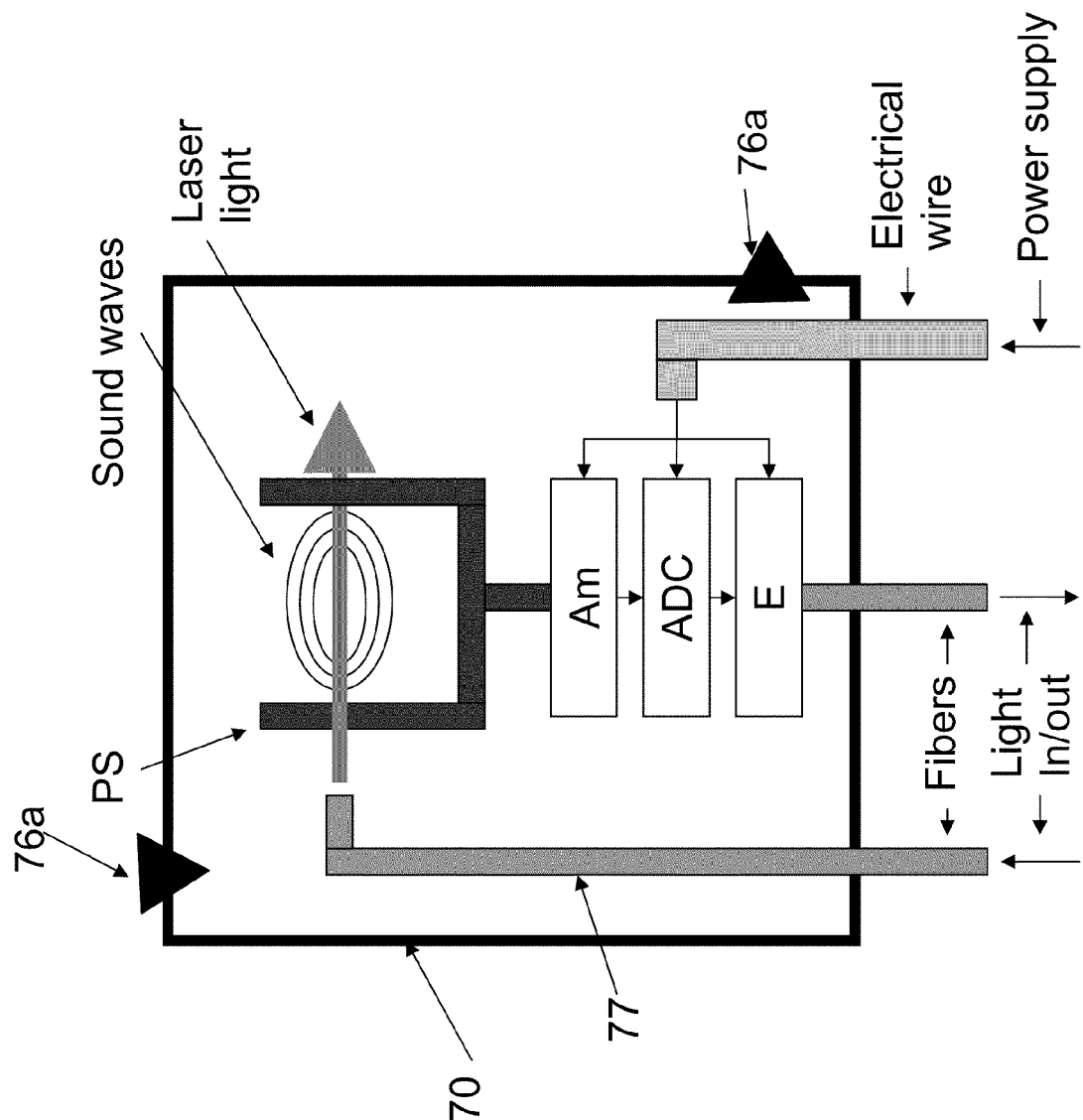
FIG. 8c is a schematic view of a similar, but not identical photoacoustic spectroscope comprising an electrical power supply in a gas sensing station and the optical fibers for optical communication with a not shown remote output system.

FIG. 8c is a schematic view of a similar, but not identical photoacoustic spectroscope comprising an electrical power supply in a gas sensing station and the optical fibers for optical communication with a not shown remote output system.

The photoacoustic spectroscope in a gas sensing station shown in FIG. 8c differs from the photoacoustic spectroscope in a gas sensing station shown in FIG. 8a in that it only comprises an electrical power supply via an electrical wire delivering energy directly to respectively the amplifier AM, the analogue-to-digital converter ADC and the light emitter E.

Figure 9:
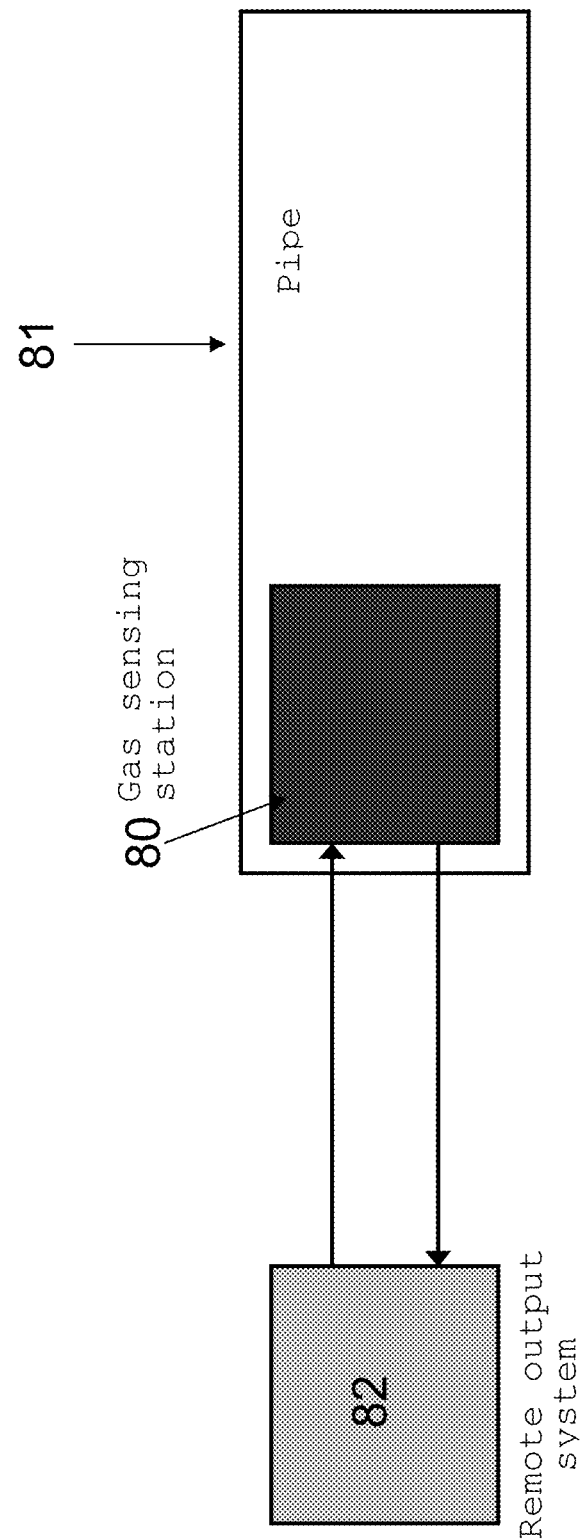
FIG. 9 is a schematic overview of a pipe system of the invention where the fluid sensing station is integrated with the pipe.

FIG. 9 is a schematic overview of a pipe system of the invention. The pipe system comprises a pipe 81, a gas sensing station 80 and a remote output system 82. The gas sensing station 80 is integrated with the pipe 81. As described and shown above, the gas sensing station 80 may preferably be integrated in the end fitting of the pipe 81. The pipe 81 comprises a not shown flow channel and a not shown annular gas cavity surrounding the flow channel. The gas sensing station comprises a not shown sensing gas cavity which is in gas communication with the annular gas cavity. The sensing gas cavity comprises a not shown photoacoustic spectroscope and optionally other elements as described above.

All energy transport between the sensing gas station 80 and the remote output system 82 is provided by optical fibers.

Figure 10:
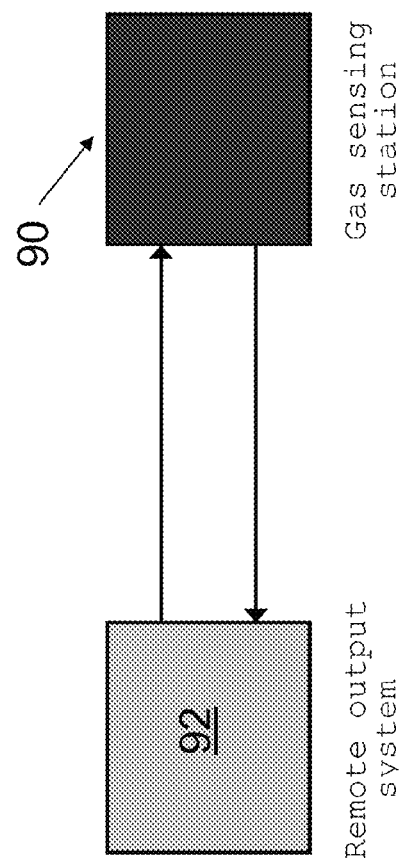
FIG. 10 is a schematic overview of a fluid sensing system of the invention comprising the remote output system in one single unit.

FIG. 10 is a schematic overview of a gas sensing system of the invention. The gas sensing system comprises a gas sensing station 90 and a remote output system 92. The gas sensing station 90 comprises a not shown sensing gas cavity comprising a not shown photoacoustic spectroscope and optionally other elements as described above.

The remote output system 92 is in one single unit and comprises a not shown light source and a not shown analyzer. The photoacoustic spectroscope is optically connected to the light source and the signal transmitted from the gas sensing station 90 is transmitted via an optical fiber to the analyzer as indicated by the arrows and as described above. The gas sensing station 90 is adapted to be connected to a pipe with an annular gas cavity to provide a gas communication between the annular gas cavity and the sensing gas cavity as described above.

All energy transport between the sensing gas station 90 and the remote output system 92 is provided by optical fibers.

Figure 11:
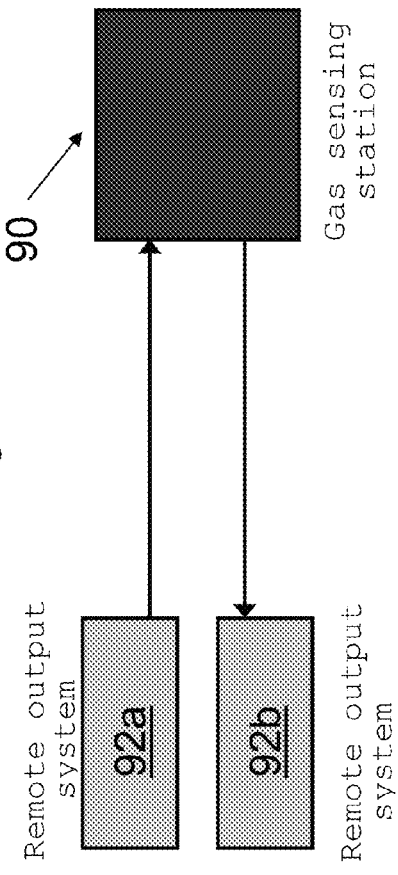
FIG. 11 is a schematic overview of a fluid sensing system of the invention comprising the remote output system in two single units.

FIG. 11 is a schematic overview of another gas sensing system of the invention. The gas sensing system comprises a gas sensing station 90 similar to the gas sensing station described for FIG. 10, and a remote output system comprising a first and a second remote output system unit 92a, 92b.

The first remote output system unit 92a comprises a not shown light source arranged to feed light to the photoacoustic spectroscope and optionally other elements in the gas sensing station 90 as indicated by the arrows and as described above. The second remote output system unit 92b comprises a not shown analyzer arranged to receive light from an optical fiber transmitting signals from the gas sensing station 90 as indicated by the arrows and as described above. The optical feeding fiber is optically connected to the light source and the optical fiber transmitting signals from the gas sensing station 90 is optically connected to the analyzer as indicated by the arrows and as described above.

All energy transport between the sensing gas station 90 and the remote output system units 92a, 92b is provided by optical fibers.

Figure 12:
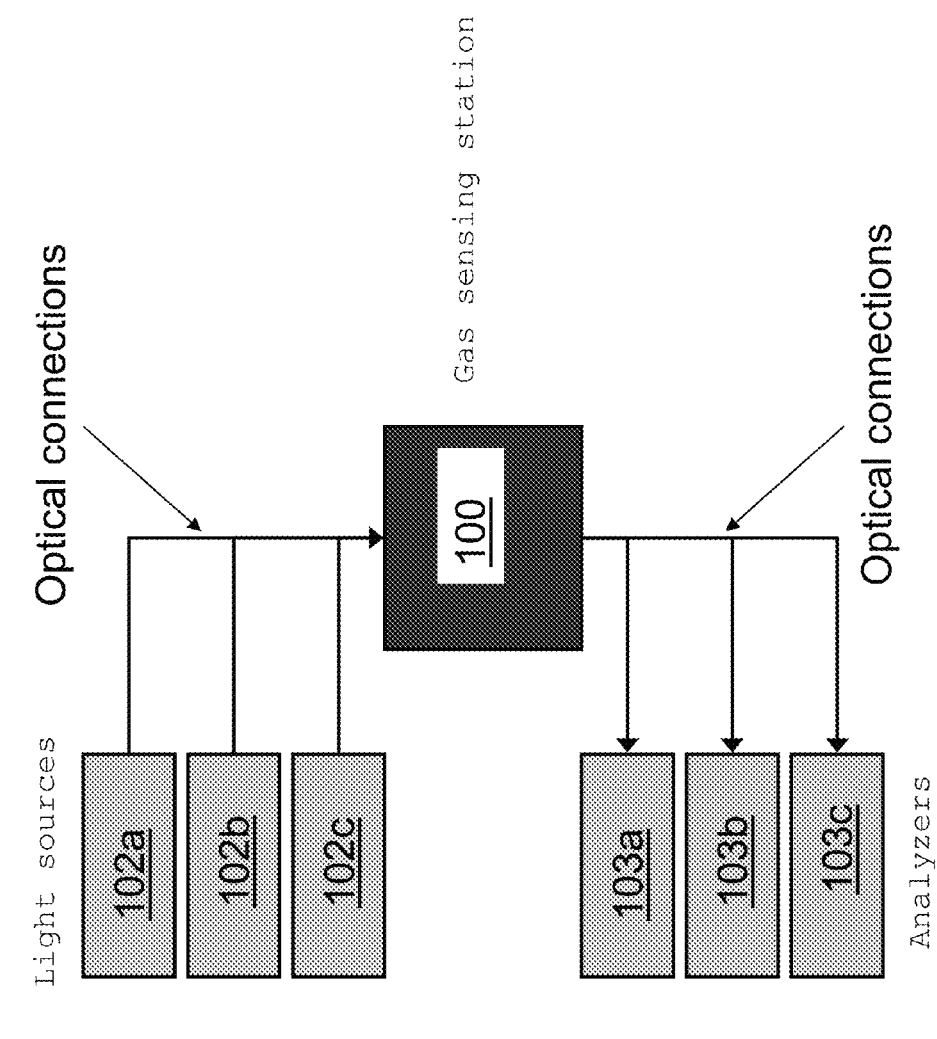
FIG. 12 is a schematic overview of a fluid sensing system of the invention comprising several light sources and several analyzers.

FIG. 12 is a schematic overview of a gas sensing system of the invention where the remote output system comprises several light sources and several analyzers. The gas sensing system comprises a gas sensing station 100 and a remote output system comprising a plurality of light sources 102a, 102b, 102c and a plurality of analyzers 103a, 103b, 103c.

The gas sensing station 100 comprises one or more not shown sensing gas cavities each comprising a not shown photoacoustic spectroscope and optionally other elements as described above.

The plurality of light sources 102a, 102b, 102c are optically connected to optical feeding fibers for feeding light and energy to the photoacoustic spectroscope and optionally energy consuming elements in the respective sensing gas cavities. Optical connectors (optical fibers) transmit signals from the gas sensing station 100 to the respective analyzers 103a, 103b, 103c. The analyzers 103a, 103b, 103c may be arranged in one remote output system unit or they may be arranged in two or more remote output system units. Each photoacoustic spectroscope is optically connected to at least one of the light sources 102a, 102b, 102c, and each analyzers 103a, 103b, 103c are optically connected to the gas sensing station 100 for receiving signals.

The gas sensing station 100 is adapted to be connected to a pipe with an annular gas cavity to provide a gas communication between the annular gas cavity and the sensing gas cavity as described above. The gas sensing station 100 may for example be provided with a face shaped to fit an outer surface of an end fitting.

All energy transport between the sensing gas station 100 and the remote output system(s) is provided by optical fibers.

Figure 13:
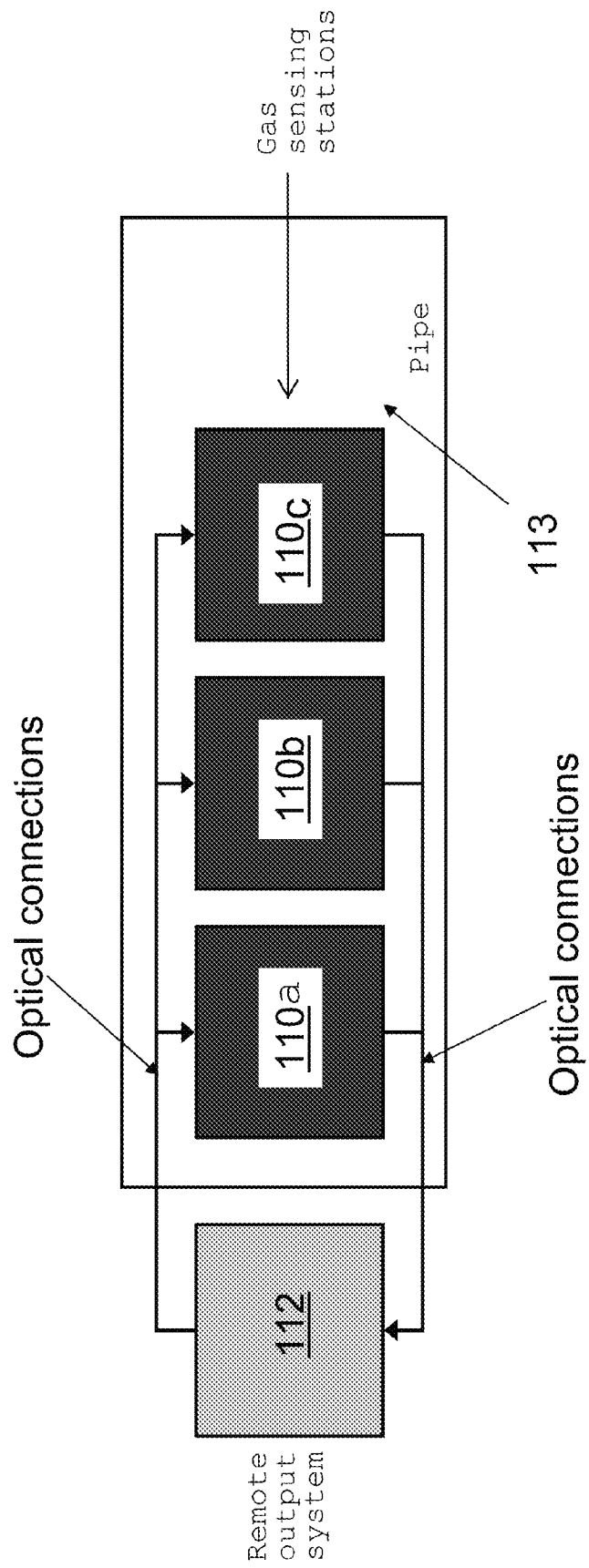
FIG. 13 is a schematic overview of a pipe system of the invention comprising several fluid sensing stations.

FIG. 13 is a schematic overview of another pipe system of the invention. The gas sensing system comprises a plurality of gas sensing stations 110a, 110b, 110c which each may be similar to the gas sensing station 90 described for FIG. 10. The gas sensing system also comprises a remote output system 112 which may be similar to the remote output system 92 described for FIG. 10.

The photoacoustic spectroscope of each of the gas sensing stations 110a, 110b, 110c is optically connected to the light source of the remote output system 112 via optical feeding fibers and the signals obtained are optically transmitted from the gas sensing stations 110a, 110b, 110c to the analyzer of the remote output system 112 as indicated by the arrows and as described above. The gas sensing stations 110a, 110b, 110c are connected to or integrated with one or more pipes 113 as described above.

All energy transport between the sensing gas sensing stations 110a, 110b, 110c and the remote output system 112 is provided by optical fibers.

Figure 14:
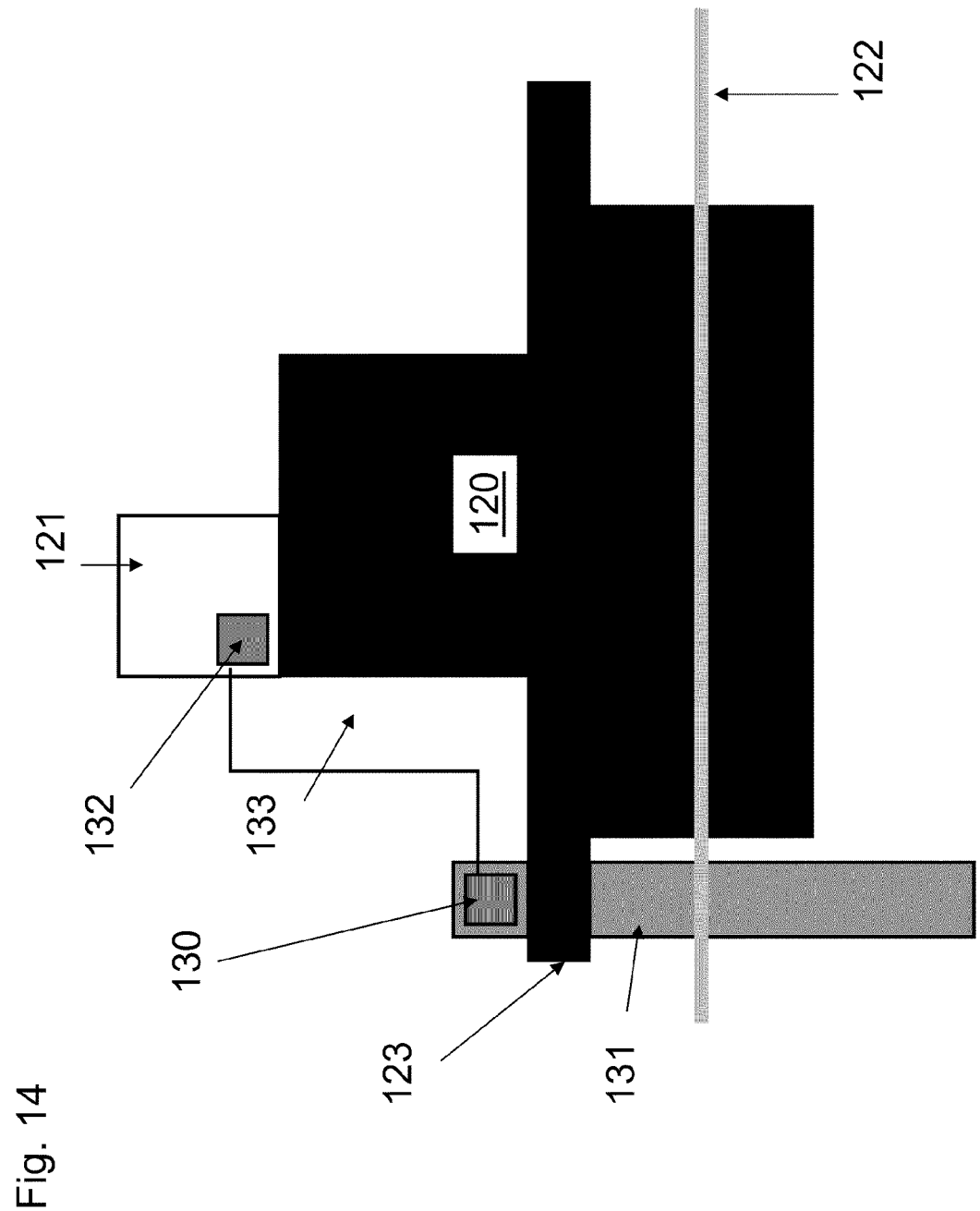
FIG. 14 is a schematic overview of a pipe system of the invention arranged in combination with a production platform.

FIG. 14 is a schematic overview of a pipe system of the invention arranged in combination with a production platform 120. The production platform 120 is an offshore platform as indicated with the waterline 122. The production platform 120 comprises a control room and an anchoring site 123 for securing a pipe. The production platform 120 may preferably also comprise a not shown tank for storing the fluid pumped up from the seabed/underground via the pipe.

The pipe system comprises a pipe 131, a gas sensing station 130 and a remote output system 132. The gas sensing station 130 is integrated with the pipe 131 in the end fitting thereof or it is fixed to the pipe 131 as described above. The pipe 131 comprises a not shown flow channel and a not shown annular gas cavity surrounding the flow channel. The gas sensing station 130 comprises a not shown sensing gas cavity which is in gas communication with the annular gas cavity. The sensing gas cavity comprises a not shown photoacoustic spectroscope and optionally other elements as described above. The gas sensing station 130 is optically connected to the remote output system via fibers 133, which should preferably provide a selected—not too small—distance between the pipe 131 and the remote output system 132 to thereby ensure a reduced risk of ignition of flammable gasses in and near the pipe. The remote output system 132 is located in the control room 121 of the production platform 120.

All energy transport between the sensing gas sensing station 130 and the remote output system 132 is provided by optical fibers.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims.

What is claimed is:

1. A pipe system comprising a pipe, a gas sensing station and a remote output system, the pipe comprises a pipe gas cavity extending lengthwise in part or all of the length of the pipe, the gas sensing station comprises a sensing gas cavity which is separated from but in gas communication with the pipe gas cavity, the sensing gas cavity comprises a photoacoustic spectroscope, the pipe system comprises at least one optical feeding fiber for feeding light to the photoacoustic spectroscope and a transmission path for transferring a signal from the photoacoustic spectroscope to the remote output system, the transmission path from the gas sensing station to the remote output system is an optical transmission path.

2. A pipe system as claimed in claim 1 wherein the pipe comprises a plurality of sheaths including an internal sheath and an outer sheath, at least two of said sheaths form a barrier against gas, the pipe gas cavity being provided between said two barrier sheaths.

3. A pipe system as claimed in claim 1 wherein said pipe gas cavity extends along the length of the pipe in a length of at least about 1 m.

4. A pipe system as claimed in claim 1 wherein the remote output system comprises at least one light source optically connected to said photoacoustic spectroscope via said at least one feeding fiber wherein said photoacoustic spectroscope comprises an acoustic detector arranged to detect gas pressure changes occurring as a result of stimulation of the gas in the photoacoustic spectroscope with light.

5. A pipe system as claimed in claim 4 wherein the light source comprises at least one of a gas discharge lamp, a laser, a light emitting diode (LED), a semiconductor diode laser, and a tunable laser.

6. A pipe system as claimed in claim 4 wherein said acoustic detector comprises at least one amplifier, the amplifier being in the form of a tuning fork comprising at least two prongs, the detection space comprises a space between said two prongs.

7. A pipe system as claimed in claim 4 wherein said acoustic detector comprises a microphone for detecting the gas pressure changes as sound waves.

8. A pipe system as claimed in claim 4 wherein said acoustic detector comprises at least one piezoelectric crystal for detecting the gas pressure changes.

9. A pipe system as claimed in claim 8 wherein said piezoelectric crystal is in electrical communication with a transducer for converting electrical signals from said piezoelectric crystal into optical signals, said optical signals being transmitted along said optical transmission path.

10. A pipe system as claimed in claim 4 comprising a transducer for converting electrical signals into optical signals, said transducer comprises an analogue-digital converter and an electromagnetic generator.

11. A pipe system as claimed in claim 1 wherein the light comprises wavelengths which are at least partly absorbable by at least one of water vapour, methane ($CH_4$), hydrogen sulphide ($H_2S$), Carbon monoxide (CO), Carbon dioxide ($CO_2$), Oxygen ($O_2$) and hydrogen ($H_2$).

12. A pipe system as claimed in claim 1 wherein said photoacoustic spectroscope comprises a detection space, said detection space being a part of or the whole sensing gas cavity of the gas sensing station, said feeding fiber being arranged to feed light to said detection space.

13. A pipe system as claimed in claim 1 wherein said photoacoustic spectroscope comprises an acoustic detector comprising a piezoelectric crystal in electrical communication with an analogue-to-digital transducer, which analogue-to digital transducer is connected to a light emitter.

14. A pipe system as claimed in claim 1 wherein the pipe system comprises at least one amplifier for amplifying the signal from the photoacoustic spectroscope, said amplifier being arranged at the gas sensing station.

15. A pipe system as claimed in claim 14 wherein said photoacoustic spectroscope comprises an acoustic detector comprising a piezoelectric crystal in electrical communication with an analogue-to digital transducer, which analogue-to digital transducer is connected to a light emitter, said amplifier being applied to amplify the electrical signal prior to converting the signal in the analogue-to digital transducer or said amplifier being applied to amplify the optical signal.

16. A pipe system as claimed in claim 1 wherein said optical feeding fiber or at least one secondary optical feeding fiber is arranged to feed light to at least one energy consuming element in said gas sensing station to provide said at least one energy consuming element with energy, said at least one energy consuming element being selected from a laser, an amplifier and a transducer.

17. A pipe system as claimed in claim 1 further comprising a power supply for supplying the photoacoustic spectroscope with electrical power, the power supply is provided via an electrical wire, said photoacoustic spectroscope comprises an acoustic detector and a detection space, said optical feeding fiber being arranged to feed light to said detection space and said electrical wire being arranged to supply energy to at least one energy consuming element, preferably selected from a laser, an amplifier and a transducer.

18. pipe system as claimed in claim 1 wherein essentially all energy transported between said remote output system and said gas sensing station is in the form of optical energy.

19. A pipe system as claimed in claim 1 wherein the remote output system comprises an analyzer, said analyzer being optically connected to said photoacoustic spectroscope for receiving optical output from said photoacoustic spectroscope.

20. A pipe system as claimed in claim 19 wherein said analyzer is capable of analyzing light from said photoacoustic spectroscope to detect the presence of water vapour or one or more of the components selected from oxygen, hydrogen, methane, hydrogen sulphides and carbon dioxides.

21. A pipe system as claimed in claim 1 wherein the remote output system comprises a light source and an analyzer, said light source and said analyzer being optically coupled such that the gas sensing station is capable of comparing the wavelengths or intensities of the emitted light with the output from the photoacoustic spectroscope.

22. A pipe system as claimed in claim 1 wherein at least one active element of the remote output system is placed at a distance from the gas sensing station which is at least about 2 m, wherein the active elements are selected from said light source and said analyzer.

23. A pipe system as claimed in claim 1 wherein the remote output system comprises at least one light source and at least one analyzer, said remote output system being optically connected to two or more gas sensing stations.

24. A pipe system as claimed in claim 23 wherein said light analyzer is optically coupled to two or more photoacoustic spectroscopes.

25. A pipe system as claimed in claim 1 wherein the pipe comprises an end fitting, said gas sensing station being integrated in said end fitting, and wherein said end fitting comprises said sensing gas cavity which is in gas communication with the pipe gas cavity.

26. A pipe system as claimed in claim 1 wherein the gas sensing station is external to the pipe.

27. A pipe system as claimed in claim 1 wherein the pipe comprises an access opening into said pipe gas cavity through which said sensing gas cavity is in gas communication with said pipe gas cavity.

28. A pipe system as claimed in claim 27 wherein the pipe comprises an end fitting, said access opening into said pipe gas cavity being provided via said end fitting.

29. A pipe system as claimed in claim 28 wherein the gas sensing station is fixed to said end fitting, by use of one or more of a snap-lock, or a bolt-nut arrangement.

30. A pipe system as claimed in claim 1 wherein said pipe is a riser pipe.

31. A pipe system as claimed in claim 30 wherein said riser comprises an end fitting for connection to an offshore station, said gas sensing station being integrated in said end-fitting or being in gas communication with said pipe gas cavity via said end-fitting and said remote output system being placed at said offshore station.

32. A gas sensing system for sensing a gas in a cavity of a pipe, said gas sensing system comprises a gas sensing station and a remote output system, said gas sensing station comprises a sensing gas cavity comprising a photoacoustic spectroscope, said remote output system comprises at least one light source and an analyzer, said at least one light source being optically connected to said photoacoustic spectroscope for feeding said photoacoustic spectroscope, said photoacoustic spectroscope further being optically connected to said analyzer for analyzing signals from said photoacoustic spectroscope, said gas sensing station being arranged to be connected to a pipe with a pipe gas cavity to provide a gas communication between said pipe gas cavity and said sensing gas cavity.

33. A gas sensing system as claimed in claim 32 wherein said at least one light source is optically connected to said photoacoustic spectroscope by at least one optical feeding fiber.

34. A gas sensing system as claimed in claim 32 wherein said system comprises an optical transmission path for transferring a signal from the photoacoustic spectroscope to the remote output system.

35. A gas sensing system as claimed in claim 32 wherein said light source comprises at least one of a gas discharge lamp, a laser, a light emitting diode (LED) and a semiconductor diode laser.

36. A gas sensing system as claimed in claim 32 wherein said gas sensing system is adapted to be connected to a pipe comprising an access opening into a pipe gas cavity, said sensing gas cavity being adapted to be in gas communication with said pipe gas cavity through said access opening.

* * * * *

UNITED STATES PATENT AND TRADEMARK OFFICE
CERTIFICATE OF CORRECTION

PATENT NO. : 8,590,365 B2  
APPLICATION NO. : 12/995740  
DATED : November 26, 2013  
INVENTOR(S) : Nicky Weppenaar et al.

Page 1 of 1

It is certified that error appears in the above-identified patent and that said Letters Patent is hereby corrected as shown below:

In the Specification, column 18, line 23, please replace "PS+ADC+FE-box" with
- PS+ADC+E -box -

Signed and Sealed this
Fourth Day of March, 2014

Michelle K. Lee
*Deputy Director of the United States Patent and Trademark Office*